(12) United States Patent
Gustafson

(10) Patent No.: US 11,911,022 B2
(45) Date of Patent: Feb. 27, 2024

(54) MINIMALLY-INVASIVE SYSTEMS AND METHODS FOR APPROXIMATING TISSUE WITH A SUTURE

(71) Applicant: MEDOS INTERNATIONAL SÀRL, Le Locle (CH)

(72) Inventor: Adam C. Gustafson, Rehoboth, MA (US)

(73) Assignee: Medos International Sarl, Le Locle (CH)

( * ) Notice: Subject to any disclaimer, the term of this patent is extended or adjusted under 35 U.S.C. 154(b) by 113 days.

(21) Appl. No.: 17/724,046

(22) Filed: Apr. 19, 2022

(65) Prior Publication Data

US 2022/0233183 A1 Jul. 28, 2022

Related U.S. Application Data

(62) Division of application No. 16/944,405, filed on Jul. 31, 2020, now Pat. No. 11,344,295.

(51) Int. Cl.
*A61B 17/04* (2006.01)

(52) U.S. Cl.
CPC ...... *A61B 17/0469* (2013.01); *A61B 17/0482* (2013.01); *A61B 2017/0474* (2013.01); *A61B 2017/0496* (2013.01)

(58) Field of Classification Search
CPC ............ A61B 17/0469; A61B 17/0482; A61B 2017/0474; A61B 2017/0496
See application file for complete search history.

(56) References Cited

U.S. PATENT DOCUMENTS

| | | | |
|---|---|---|---|
| 5,178,629 A | 1/1993 | Kammerer | |
| 5,222,508 A | 6/1993 | Contarini | |
| 5,281,237 A | 1/1994 | Gimpelson | |
| 5,501,691 A | 3/1996 | Goldrath | |
| 5,658,299 A * | 8/1997 | Hart | A61B 17/12013 606/139 |
| 5,722,981 A | 3/1998 | Stevens | |
| 7,625,386 B2 | 12/2009 | Abe et al. | |
| 8,075,572 B2 | 12/2011 | Stefanchik et al. | |

(Continued)

OTHER PUBLICATIONS

U.S. Appl. No. 16/944,405, filed Jul. 31, 2020, Minimally Invasive Systems and Methods for Approximately Tissue With a Suture.

(Continued)

*Primary Examiner* — Phong Son H Dang

(57) ABSTRACT

A minimally invasive surgical method of approximating tissue includes coupling an adjustable loop of suture around an inserter. The loop can be coupled to the inserter by applying tension to a tail of the suture to collapse the loop around the inserter, then the inserter and loop are passed through a first location in tissue. The loop is decoupled from the inserter, the inserter is retracted from the first location, and reinserted into a second location in the tissue, after which the loop is recoupled to the inserter while the loop is distal of the tissue. The decoupling, retraction, and reinsertion can occur without withdrawing the inserter from the patient's body. The inserter and loop are then withdrawn together from the tissue through this second location and outside of the patient's body. The tails and loop can form a luggage knot to be reduced around the tissue.

6 Claims, 22 Drawing Sheets

(56) References Cited

U.S. PATENT DOCUMENTS

| | | | |
|---|---|---|---|
| 8,460,322 B2* | 6/2013 | van der Burg | A61B 17/0469 |
| | | | 606/144 |
| 8,672,955 B2* | 3/2014 | Nagata | A61B 17/0482 |
| | | | 606/139 |
| 9,055,940 B2 | 6/2015 | Chin | |
| 9,492,158 B2* | 11/2016 | Stone | A61F 2/0811 |
| 9,782,162 B2 | 10/2017 | Levin et al. | |
| 9,936,941 B2 | 4/2018 | Weisel et al. | |
| 10,034,752 B2 | 7/2018 | Taylor | |
| 10,258,320 B2* | 4/2019 | Dreyfuss | A61B 17/0401 |
| 10,575,842 B2* | 3/2020 | Lund | A61L 31/048 |
| 11,096,682 B2 | 8/2021 | Foerster et al. | |
| 11,259,794 B2* | 3/2022 | Stone | A61B 17/0482 |
| 11,529,134 B2* | 12/2022 | Taylor | A61B 17/0401 |
| 11,612,391 B2* | 3/2023 | Stone | A61B 17/0482 |
| | | | 606/139 |
| 2004/0087978 A1 | 5/2004 | Velez et al. | |
| 2007/0179509 A1 | 8/2007 | Nagata et al. | |
| 2009/0228041 A1 | 9/2009 | Domingo | |
| 2011/0029000 A1 | 2/2011 | Lavi et al. | |
| 2011/0245850 A1 | 10/2011 | van der Burg et al. | |
| 2012/0123448 A1 | 5/2012 | Flom et al. | |
| 2012/0191109 A1 | 7/2012 | Rockrohr | |
| 2013/0090670 A1 | 4/2013 | Keating et al. | |
| 2013/0190818 A1* | 7/2013 | Norton | A61B 17/0401 |
| | | | 606/232 |
| 2015/0012094 A1 | 1/2015 | Denham et al. | |
| 2016/0317306 A1 | 11/2016 | Taylor | |
| 2018/0280016 A1 | 10/2018 | Krespi et al. | |
| 2022/0096081 A1* | 3/2022 | Denham | D04C 1/06 |
| 2022/0233183 A1 | 7/2022 | Gustafson | |

OTHER PUBLICATIONS

Extended European Search Report for Application No. 21188837.5 dated Dec. 15, 2021 (9 pages).

* cited by examiner

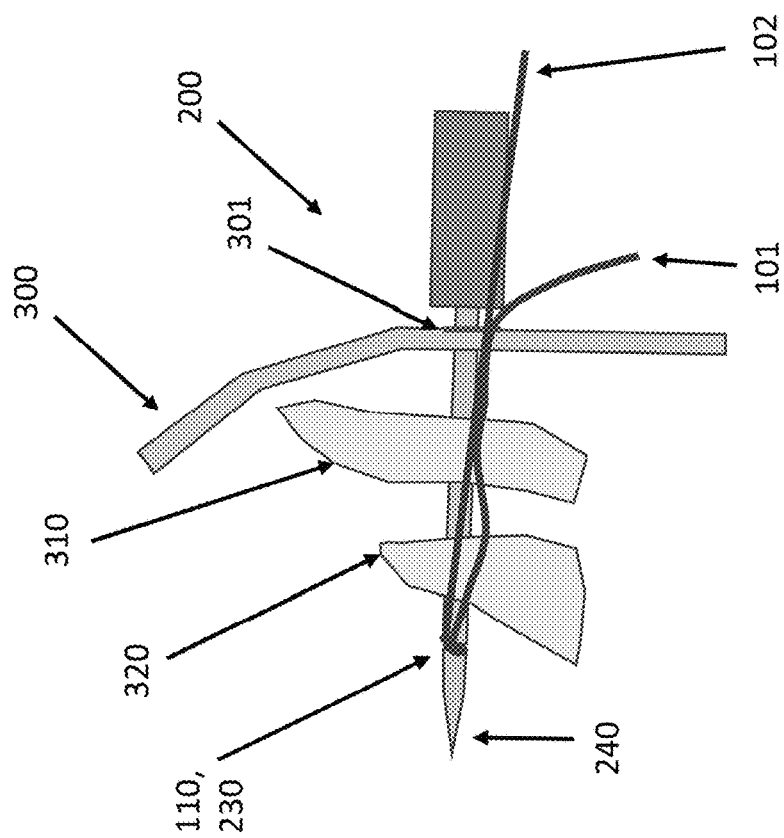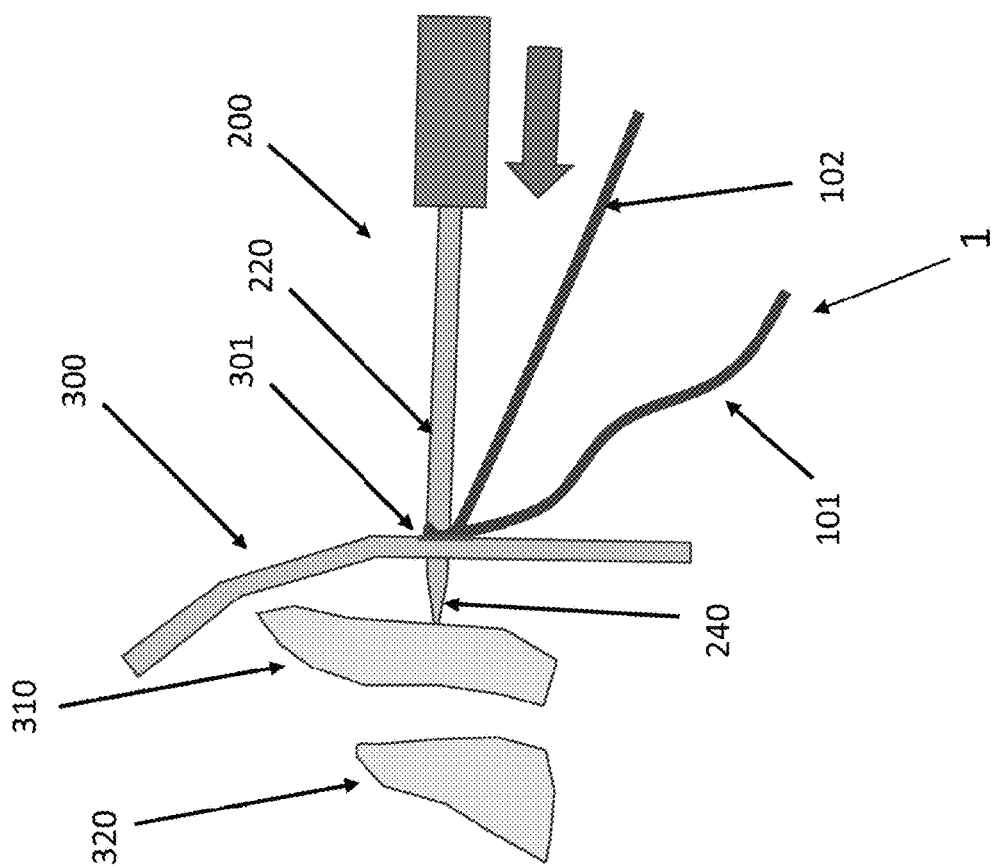
FIG. 3B
FIG. 3A

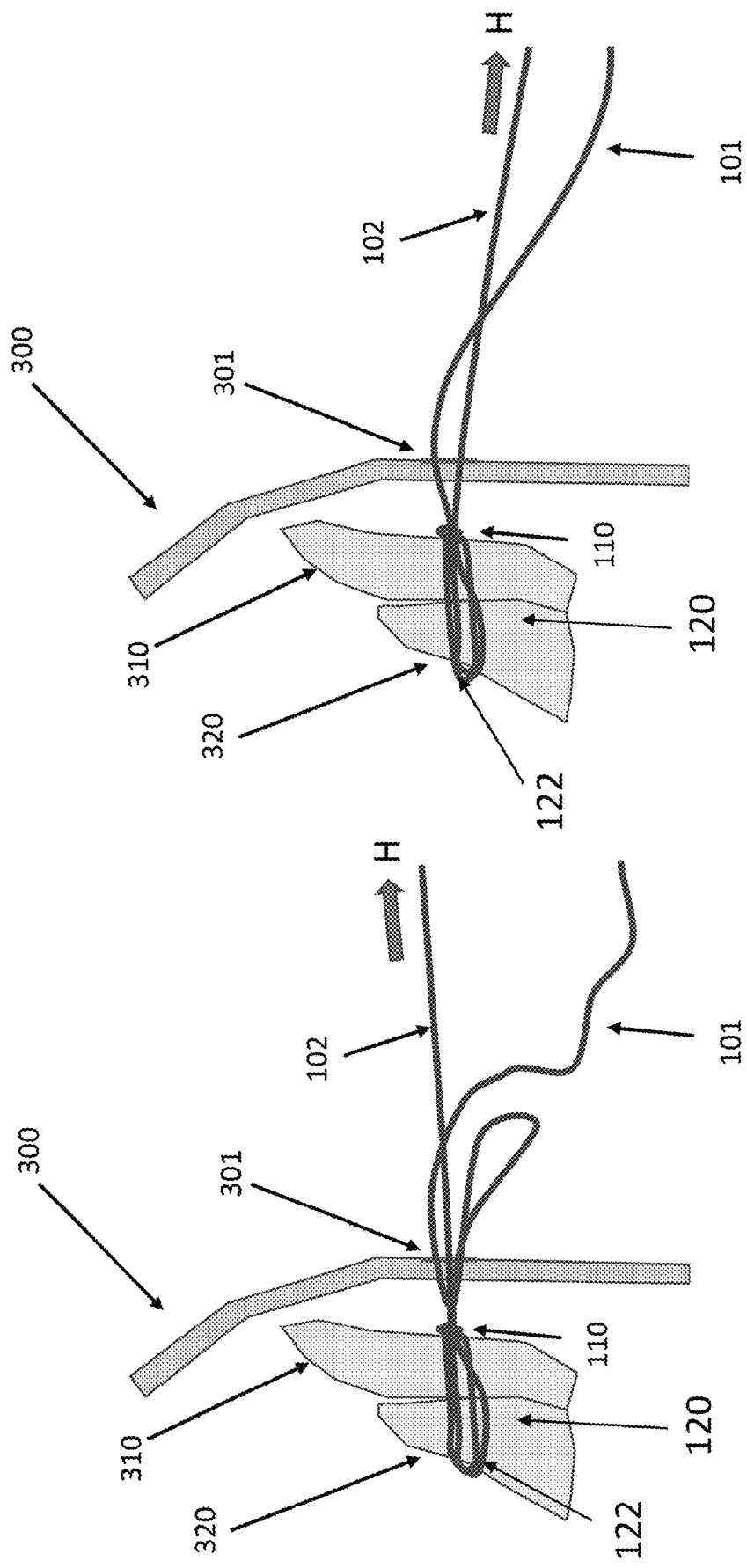

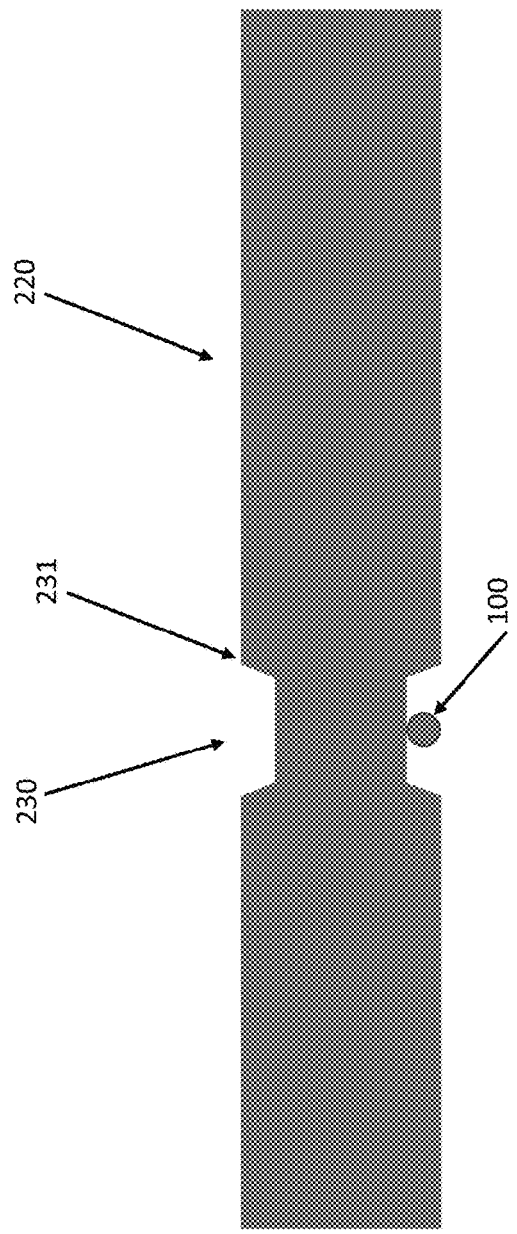
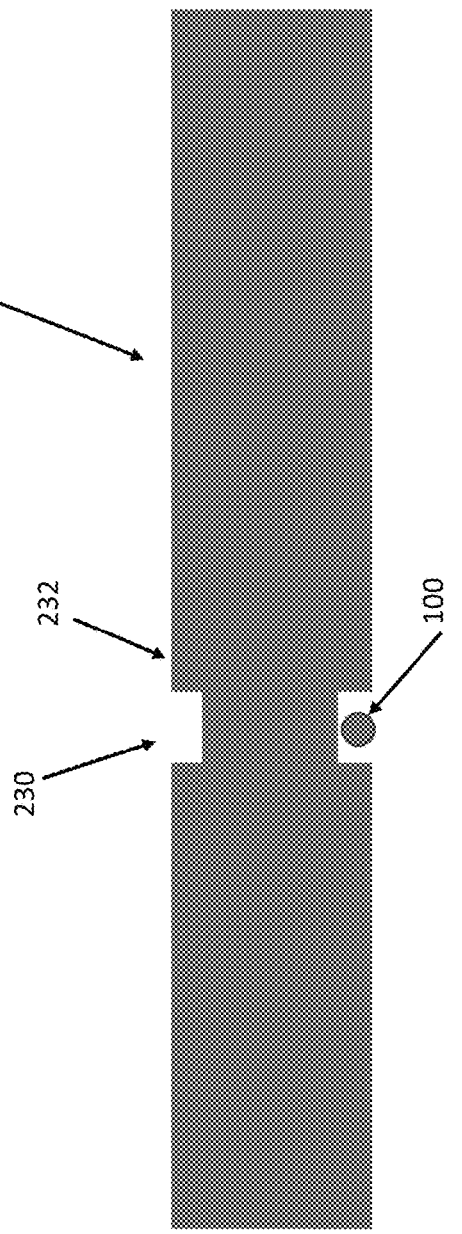
FIG. 4
FIG. 5

MINIMALLY-INVASIVE SYSTEMS AND METHODS FOR APPROXIMATING TISSUE WITH A SUTURE

CROSS-REFERENCE TO RELATED APPLICATIONS

This application claims the benefit of and is a division of U.S. patent application Ser. No. 16/944,405, filed Jul. 31, 2020, which is hereby incorporated by reference in its entirety.

FIELD

The present disclosure relates to systems, devices, and methods for securing soft tissue together, and more particularly relates to systems, devices, and methods for approximating tissue with a mattress stitch and luggage tag knot through a single incision without needing to establish a subcutaneous plain to retrieve the suture limbs during, for example, meniscal repair and soft tenodesis of the long head of the biceps.

BACKGROUND

A common injury, especially among athletes and people of advancing age, is the complete or partial tear of tendons, ligaments, or other soft tissues. Soft tissue tears may occur during a fall, by overexertion, or for a variety of other reasons. Surgical intervention is often needed, particularly when tissue is partially or completely torn. Currently available devices for tissue attachment include screws, staples, suture anchors, and tacks. Currently available devices for patients of advancing age can be particularly insufficient due to degenerated tissue leading to inadequate suture-to-anchor fixation and further damage to the soft tissue.

There is a desire with these types of injuries to operate in a minimally invasive manner. Current techniques for passing a mattress stitch (e.g., during an inside-out meniscal repair) typically require establishing a subcutaneous plain to allow retrieval and tying of the suture limbs without capturing superficial tissue in the repair. Additionally, in current procedures the surgeon typically must tie a series of knots that can require several throws to achieve the desired strength and security. It is desirable to reduce this knot stack to alleviate repetitive work, the complexity of tying a proper knot, reduce the potential for interference or harm to tissue based on the space consumed by the knot stack, and to reduce the material implanted in the patient.

Accordingly, there is a need for improved systems, methods, and devices for minimally invasive method for approximating tissue in an accurate, more efficient, and less disruptive manner by using a single incision and minimal disruption to the target tissue.

SUMMARY

Embodiments of the present disclosure provide for minimally invasive methods for approximating tissue with a mattress stitch through a single incision without needing to establish a subcutaneous plain to retrieve the suture limbs. A luggage tag knot configuration is often used in conjunction with the procedure, although other knot configurations can be used without departing from the spirit of the present disclosure. Embodiments of this method may be generally applied were advantageous, for example with meniscal repair and soft tenodesis of the long head of the biceps.

In some embodiments of the present disclosure a suture filament is pierced through itself, or threaded through an eyelet defined by a bifurcate braided portion, to create a loop or snare portion, also referred to as an adjustable loop. This suture filament construct, sometimes referred to herein as a shackle, creates two limbs: an inner limb created by the end that pierced through the suture, and an outer limb associated with the section of the suture that was pierced. Pulling on the inner limb can tighten or close the loop portion, while applying tension to the outer limb can loosen or open the loop portion. An inserter can be provided for use with the suture filament, the inserter having a needle-like distal end with a reduced diameter section near the tip for engagement with the adjustable loop, as described in more detail herein.

In an example operation, the adjustable loop of the suture filament is tightened around the reduced diameter portion on the inserter by pulling on the inner limb of the suture filament. Thereafter, with tension being held on the inner limb, the inserter can be introduced into a single incision of a patient and passed through a soft tissue and/or cartilage that is to be approximated, creating a first opening. With the inserter and suture filament disposed through the soft tissue, the tension on the inner limb can be removed and tension can be applied to the outer limb of the suture filament to disengage the adjustable loop from the reduced diameter section of the inserter. The inserter can be retracted part way from the patient, now without the suture filament collapsed on it, and a second bite of the soft tissue can be taken by re-inserting the inserter through the soft tissue at a separate location, thus creating a second opening without creating a second incision. A distal tip of the inserter can be driven through the adjustable loop and tension can be applied to the inner limb to tighten the adjustable loop around the reduced diameter of the inserter. With some tension being maintained in the inner limb, the inserter can be withdrawn from the patient through the second opening, drawing the suture filament further through both the first and second openings. With the inserter removed from the soft tissue, the outer limb can be used to enlarge the loop and the inserter can be decoupled of otherwise disengaged from the suture filament. The tails of the suture filament can be fed through the loop to create a luggage knot, thereby capturing the soft tissue, and the tails can be tensioned using the inner limb, and then the outer limb, to reduce a diameter of a loop formed by the luggage knot and approximate the tissue. Thereafter, one or more half-hitch knots can tied and tensioned using the inner limb as the post for final tension and security of the repair.

One exemplary embodiment of a surgical method includes inserting an inserter having a suture filament coupled to it through an incision and through at least a first target tissue. The inserter draws lengths of a first tail and a second tail of the suture filament through a first opening in the first target tissue. The method further includes decoupling the adjustable loop of the suture filament from the inserter such that the adjustable loop defines an adjustable opening of the loop. After the adjustable loop is decoupled from the inserter, the inserter is withdrawn from the first opening in the target tissue. Further, the method includes inserting the inserter through a second opening in the first target tissue and through the adjustable opening of the adjustable loop. The adjustable loop is recoupled to the inserter by collapsing the adjustable loop around the inserter. After recoupling the adjustable loop to the inserter, the inserter is withdrawn from the second opening in the first target tissue, the inserter drawing lengths of the first and second tails of the suture filament through the second opening. After the inserter is withdrawn from the second opening, the adjustable loop is decoupled from the inserter. The target tissue can include, for example, a tendon or cartilage.

In some embodiments, after the inserter is withdrawn from the second opening and the adjustable loop is decoupled from the inserter, tension can be applied to the suture filament to move a location of the first tissue with respect to at least one of a second tissue, bone, or another object disposed in a body of a patient in which the first tissue is disposed. The method can also include passing the first and second tails of the suture filament through the adjustable loop and collapsing the adjustable loop around the first and second tails. In such instances, applying tension to the suture filament to move a location of the first tissue with respect to at least one of a second tissue, bone, or other object disposed in a body of a patient in which the first tissue is disposed can include applying tension to one of the first and second tails to advance the collapsed adjustable loop towards the first tissue to move the location of the first tissue with respect to at least one of a second tissue, bone, or other object disposed in a body of a patient in which the first tissue is disposed. This application of tension can result, for example, in the first tissue being drawn closer to the second tissue. In some embodiments, the method can include setting a location of the collapsed adjustable loop by tying one or more knots with the first and second tails.

When performing the method, at least a portion of a distal end of the inserter can remain disposed in a body of a patient in which the first tissue is disposed from between when the inserter is inserted through the incision through at least the first target tissue until withdrawing the inserter from the second opening. This can result in the distal end of the inserter not being withdrawn from superficial tissue disposed proximate to the first tissue during that time. In some embodiments, the superficial tissue can include a skin layer.

Prior to inserting the inserter having a suture filament coupled to it through an incision, the method can include positioning the inserter through the adjustable opening defined by the adjustable loop and collapsing the adjustable loop around the inserter to couple the suture filament to the inserter. A distal end of the inserter can include a needle. In such embodiments, the method can include forming the first opening in the first target tissue as the inserter is inserted through the first target tissue, and/or forming the second opening in the first target tissue as the inserter is inserted through the first target tissue. Further, the inserter can include a coupling region that is configured to retain the adjustable loop at a desired location with respect to the inserter when the adjustable loop is collapsed around the inserter. By way of non-limiting example, the coupling region can include a reduced diameter section that can be formed in an outer surface of the inserter.

In some embodiments, the action of decoupling the adjustable loop of the suture filament from the inserter can include applying tension to one of the first and second tails to increase a diameter of the opening defined by the adjustable loop. The second tail can, at least in some instances, pass through the first tail to form the adjustable loop of the suture filament such that the second tail is slidably disposed within the first tail. The method can also include applying tension to at least one of the first and second tails during the action of withdrawing the inserter from the second opening in the first target tissue. This can help to maintain the coupling of the suture filament to the inserter during insertion. Tension can also be applied to at least one of the first and second tails during the action of inserting the inserter through the incision and through the first target tissue to draw lengths of the first and second tails through the first opening, again to help maintain the coupling of the suture filament to the inserter during insertion.

One exemplary embodiment of a surgical repair system includes a suture construct formed from a suture filament and an inserter. The suture construct includes a first tail, a second tail, and an adjustable loop. An opening of the adjustable loop is defined by the second tail being slidably disposed within the first tail such that applying tension to the second tail collapses the opening of the adjustable loop. The inserter includes a proximal handle, a coupling region, and a distal end. The distal end includes a needle, and the coupling region is configured to retain the adjustable loop at the coupling region during insertion of the needle through a target tissue when the adjustable loop is collapsed around the coupling region.

In some embodiments, the first tail can include an eyelet formed in it and the second tail can be slidably disposed through the eyelet. In some embodiments the suture filament can be a braided suture. In such instances the braided suture can be bifurcated at a location at which the second tail is slidably disposed within the first tail.

The coupling region of the inserter can include a reduced diameter section of an outer surface of the inserter. In some such embodiments the reduced diameter section can define at least one of a proximal transition section or a distal transition section having a chamfered edge disposed between two different diameter sections of the inserter. In some embodiments, the first tail and the second tail can be part of a single length of the suture filament.

BRIEF DESCRIPTION OF DRAWINGS

This disclosure will be more fully understood from the following detailed description taken in conjunction with the accompanying drawings, in which:

FIGS. 3A-3L provide for a schematic illustration of one exemplary embodiment of a surgical procedure using the suture filament of FIG. 1A and the inserter of FIG. 1B;

FIG. 3A is a schematic top view illustrating the inserter and suture filament in the arrangement of FIG. 2B being introduced to a surgical site through a single incision in a patient's skin;

FIG. 3B is a schematic top view illustrating the inserter and suture filament being passed through a first location in a soft tissue;

FIG. 3C is a schematic top view illustrating the adjustable loop of the suture filament being expanded to decouple the suture filament from the inserter after both are passed through the soft tissue;

FIG. 3D is a schematic top view illustrating the inserter being removed from soft tissue, leaving the suture filament disposed through the first location in the soft tissue;

FIG. 3E is a schematic top view illustrating the inserter being passed through a second location in the soft tissue;

FIG. 3F is a schematic top view illustrating the inserter being passed through the adjustable loop of the suture filament;

FIG. 3G is a schematic top view illustrating the suture filament coupled to the insert by way of the adjustable loop being collapsed onto the insert and the inserter being withdrawn from the second location in the soft tissue;

FIG. 3H is a schematic top view illustrating the adjustable loop being expanded and decoupled from the inserter by applying tension to the outside tail of the suture filament;

FIG. 3I is a schematic top view illustrating a luggage tag knot being tied in the suture filament by passing the inner and outer tails of the suture filament through the adjustable loop;

FIGS. 3J and 3K are schematic top views illustrating an adjustable loop formed by the luggage tag knot being collapsed to draw the soft tissue together;

FIG. 3L is a schematic top view illustrating the formation of one or more halt-hitches in the suture filament to secure a location of the suture filament with respect to the soft tissue, trimming the inner and outer tails of the suture filament, and closing the incision;

FIG. 4 is a schematic top view of one exemplary embodiment of a reduced diameter section of an inserter;

FIG. 5 is a schematic top view of another exemplary embodiment of a reduced diameter section of an inserter;

DETAILED DESCRIPTION

Figure 1A:
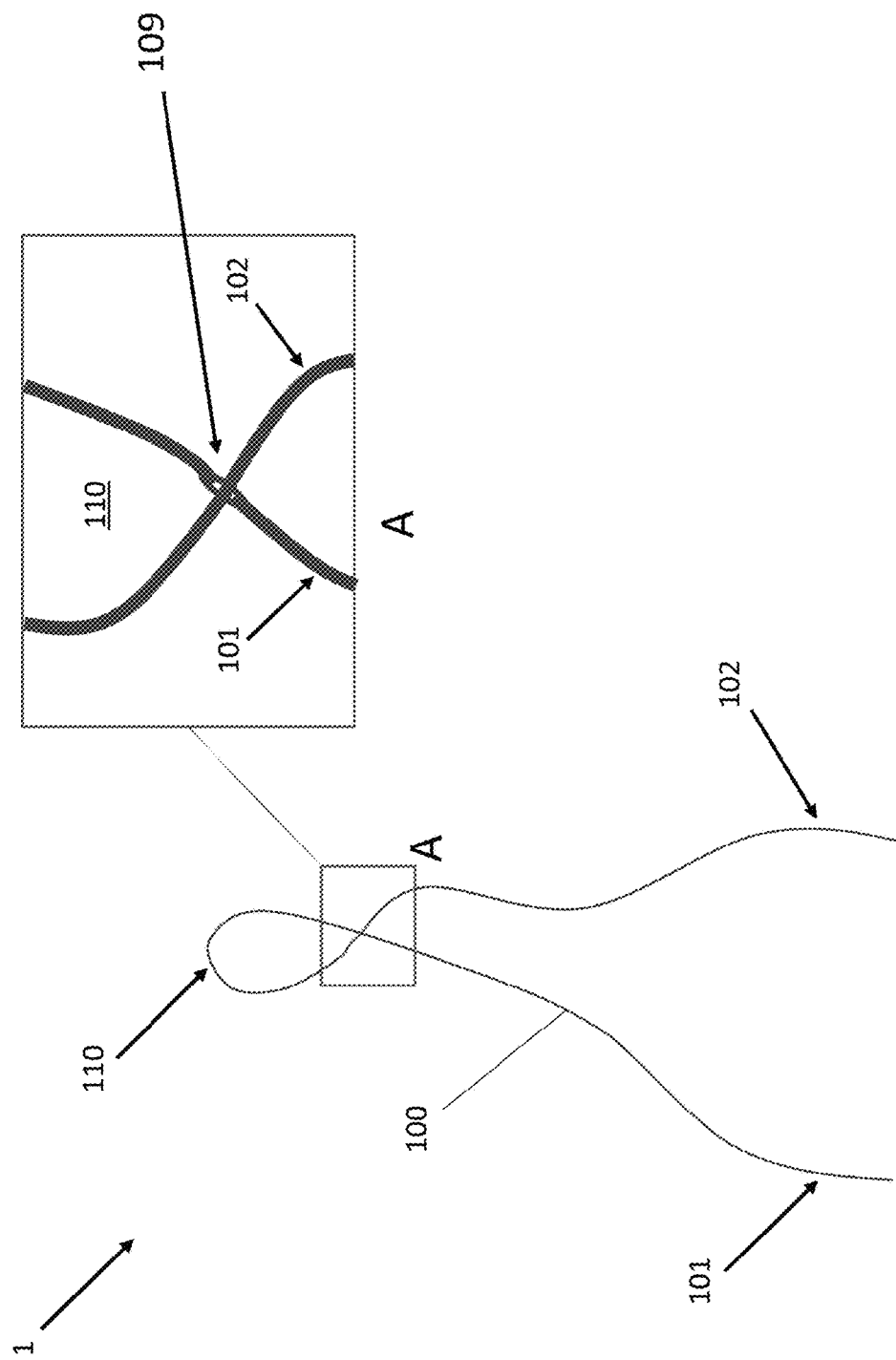
FIG. 1A is a top view of one exemplary embodiment of a suture construct that includes a suture filament having an outside tail and inside tail forming an adjustable loop with the inside tail passing through the outside tail.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

In the present disclosure, like-numbered components of the embodiments generally have similar features. Still further, sizes and shapes of the systems, and the components thereof, can depend at least on the anatomy of the subject in which the systems will be used, the size and shape of components with which the devices will be used, and the methods and procedures in which the devices will be used.

To the extent the illustrated embodiments and accompanying descriptions make reference to a specific surgery, the systems and methods described herein can be utilized in various applications involving robotic, robot-assisted, and non-robotic operations where minimally invasive tissue approximation may be required. Example applications include meniscal repair and soft tenodesis of the long head of the biceps, wherein the anatomical structure to approximated can be meniscal tissue or one or more tendons. Other procedures with which the present systems and techniques can be used include capsule repairs, AC joint repairs, attaching bone to the labrum. The teachings of the present disclosure can be applied to such procedures, however, the systems and methods described herein are not limited to these applications. Additionally, to the extent that terms are used in the disclosure to describe a direction, orientation, and/or relative position of the disclosed constructs and other instruments and tools, such terms are not intended to be limiting. For example, a person skilled in the art will recognize that terms of direction, orientation, and/or relative position (e.g., proximal, distal, etc.) can be used interchangeably depending, at least in part, on the perspective view of the surgeon or other operator.

The figures provided herein are not necessarily to scale. Further, to the extent arrows are used to describe a direction a component can be tensioned or pulled, these arrows are illustrative and in no way limit the direction the respective component can be tensioned or pulled. A person skilled in the art will recognize other ways and directions for creating the desired tension or movement. As provided for herein, the terms force and tension may be used interchangeably, and a person skilled in the art will appreciate the distinctions and similarities between these two terms. Thus, for example, to the extent the present application describes applying a tension or the existence of tension, typically the term force can be used in its place. Likewise, while in some embodiments movement of one component is described with respect to another, a person skilled in the art will recognize that other movements are possible. Additionally, although terms such as "first" and "second" are used to describe various aspects of a component, e.g., a first end and a second end, such use is not indicative that one component comes before the other. Use of terms of this nature may be used to distinguish two similar components or features, and often such first and second components can be used interchangeably. Still further, a number of terms may be used throughout the disclosure interchangeably but will be understood by a person skilled in the art. By way of non-limiting example, the terms "suture" and "filament" may be used interchangeably.

Surgical repair constructs and methods for soft tissue repair are generally provided and they generally involve the use of surgical filaments, referred to herein more broadly as surgical constructs or shackles, that are configured in a variety of manners to minimize and/or eliminate the tying of knots during a surgical procedure while also minimizing the amount of trauma imparted by the constructs to tissue with which the constructs are used and/or other tissue or the like in the body. The constructs described herein provide superior strength for use in a number of different surgical procedures, such as meniscal repair and soft tenodesis of the long head of the biceps, along with other types of tendon and tissue repair procedures. The designs of the constructs described herein are such that they can be easily coupled and decoupled from an inserter multiple times, even when the location of where the filament couples to the inserter is at a surgical site in the body. The coupling and decoupling can be controlled outside of the body, such as by applying tension to the different tails of the construct. The ability to pass a suture loop through tissue and approximate the tissue with minimal trauma results from the ability to pass the suture through a first opening in the tissue, and subsequently retrieve the suture through a second opening, with only two corresponding insertions of an inserter though the tissue. This can all be performed through a single, minimally invasive incision in the body.

FIGS. 1A, 1B, 2A, and 2B show an overview of one embodiment of a surgical system according to the present disclosure, including a suture filament 100 and an inserter 200. FIG. 1C provides for an alternative embodiment of an inserter 200'.

FIG. 1A provides for one exemplary embodiment of a suture filament construct or shackle 1. The construct 1 includes a suture filament 100 having an outside or outer tail 101, also referred to as a first tail, and inside or inner tail 102, also referred to as a second tail, that form an adjustable loop 110. As shown in Detail A, the inside tail 102 passes through the outside tail 101. Here, the outside tail 101 is shown to have an opening 109 through the filament where the inside tail 102 has been passed through to allow the inside tail 102 to freely move with respect to the opening 109 to expand or shrink the adjustable loop 110. In operation, applying tension to the inside tail 102 will shrink the adjustable loop 110 and, with the adjustable loop 110 securely tightened around an object, applying tension to the outside tail 101 will urge the opening 109 away from the object and expand the adjustable loop 110. One skilled in the art will appreciate that these suture structures may be referred to interchangeably by different names, such as the adjustable loop 110 also being referred to as a loop portion or a snare. Similarly, the tails may also be referred to as limbs or generally lengths or portions (e.g., first portion, second portion) of a suture filament. Although in the illustrated embodiment of FIG. 1A the adjustable loop 110 is formed by inserting the inner tail 102 into an opening 109 in the outer tail 101, a person skilled in the art will understand other ways by which this junction can be formed without departing from the spirit of the present disclosure. By way of non-limiting examples, the opening 109 can be formed generally as a passage through the suture filament 100, which can include a piecing through the suture filament 100, a bifurcation that is formed in the suture filament 100, such as when the filament is a braided filament, or other techniques known to those skilled in the art for passing filament through filament.

Figure 1B:
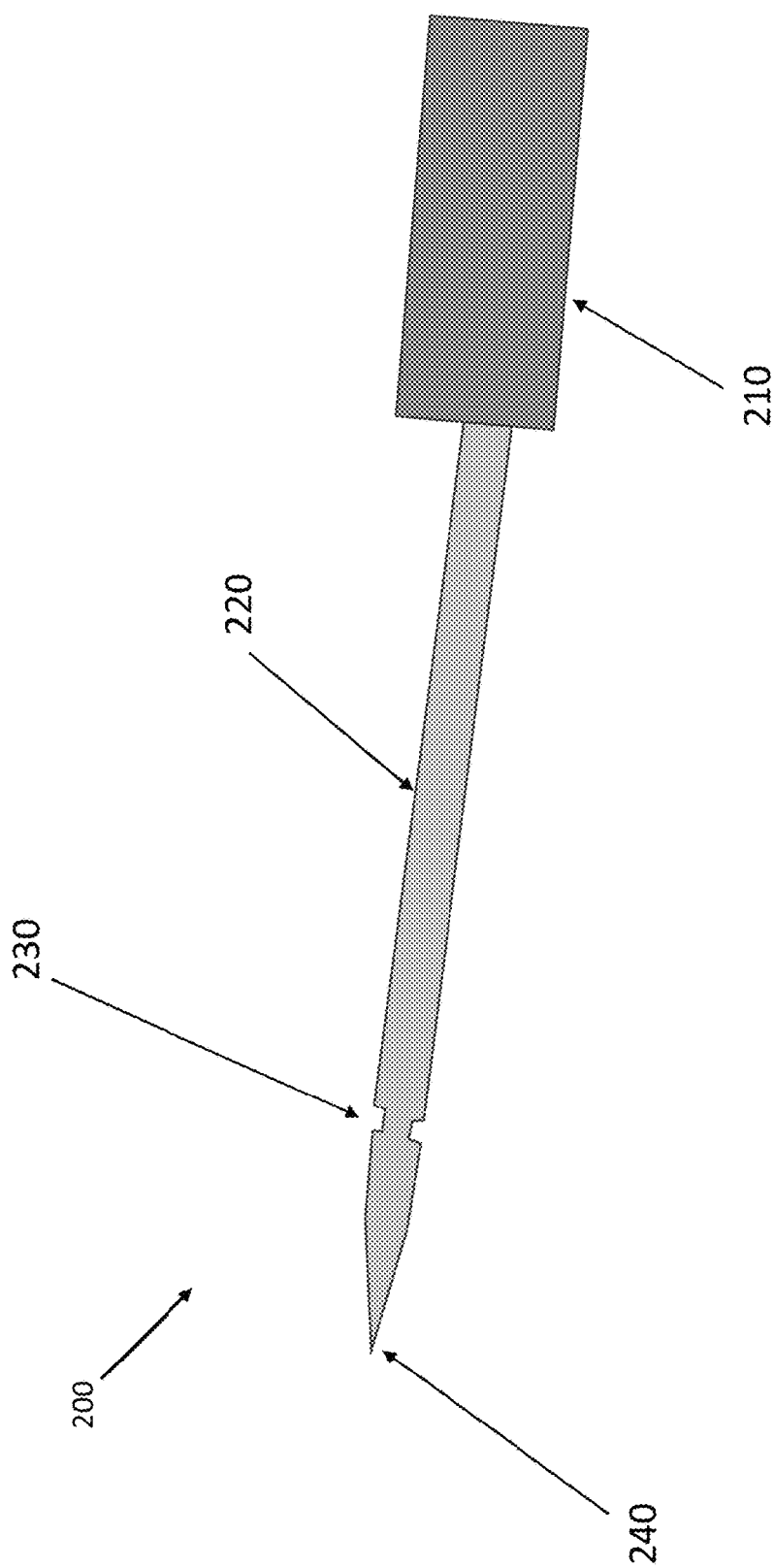
FIG. 1B is a schematic top view of one exemplary embodiment of an inserter having a distal needle and a reduced diameter section.
Figure 1C:
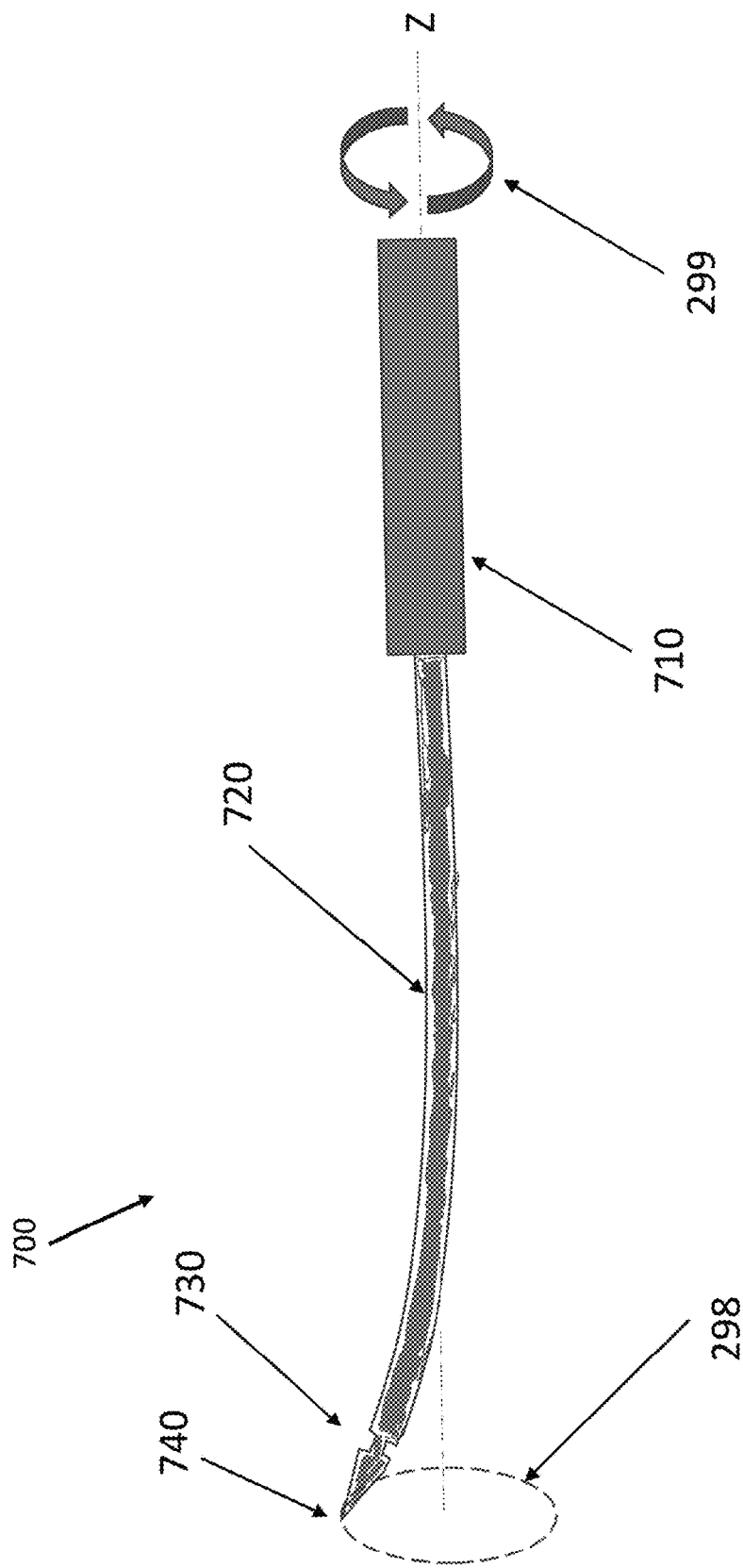
FIG. 1C is a schematic top view of another exemplary embodiment of an inserter having a distal needle and a reduced diameter section.

FIG. 1B is a schematic illustration of an exemplary embodiment of an inserter device 200 having a generally elongate body with a distal end including a distal needle 220 and a proximal end including a handle or handle portion 210. The distal needle 220 terminates at a sharp, tissue-penetrating tip 240 and also includes a coupling region or feature 230 located on an outer surface of the inserter, as shown a reduced diameter section, formed in the outer surface along a length of the distal needle. In some embodiments, the coupling region or feature 230 does not have (although it may have) a reduced diameter, and includes one or more features configured to retain an adjustable loop section of a suture filament at a designated location on the inserter 200, such as a protrusion (e.g., a shelf on which the filament can sit) or texture (e.g., contours configured to grip or otherwise hold filament at a designated location on the inserter 200). A person skilled in the art will recognize that the inserter 200 is illustrated schematically such that it provides for a simplified version of an inserter. In practice and use, typically the inserter 200 will have additional and/or more pronounced features. For example, the handle portion 210 may have grooves or other gripping features that help a user handle and control the inserter 200. The device may include additional mechanical or electronic features that can enhance the ability to control the inserter 200.

FIG. 1C shows another embodiment of an inserter that is a curved inserter 700 having a distal needle 720 with a reduced diameter section 730 and a sharp tissue-penetrating tip 740, the distal needle 720 extending from a handle portion 710. The distal needle 720 can be curved and/or have selective flexibility, based on materials (e.g., shape-memory materials like nitinol) and/or the construction of the needle 720. Curvature in the distal needle 720, or the ability to be selectively curved during use, can allow for a degree of placement when off-loading and capturing the construct 1 by rotating the handle 710 about a longitudinal axis Z, as shown by rotation 299 of the handle 710 inducing circular movement 298 of the sharp tissue-penetrating tip 740.

Figure 2A:
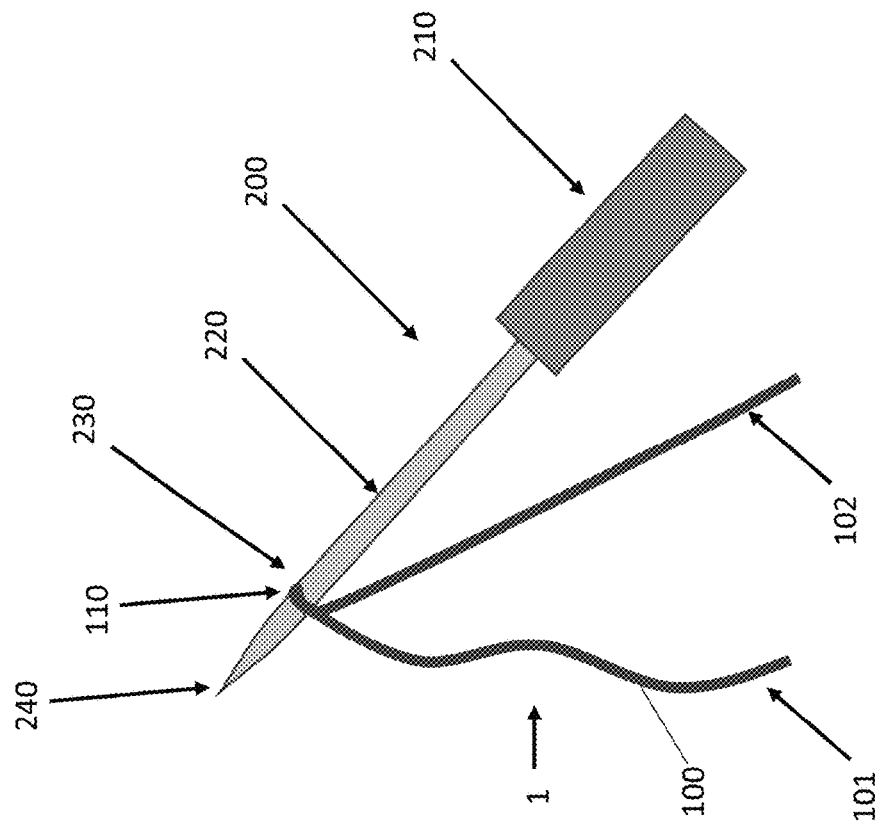
FIGS. 2A and 2B provide for a schematic illustration of one exemplary embodiment of the adjustable loop of the suture construct of FIG. 1A being coupled to the inserter of FIG. 1B, with FIG. 2A being a top view of the inserter being passed through the adjustable loop of the suture filament, and FIG. 2B being a top view of the adjustable loop being collapsed around the reduced diameter section of the inserter.
Figure 2B:
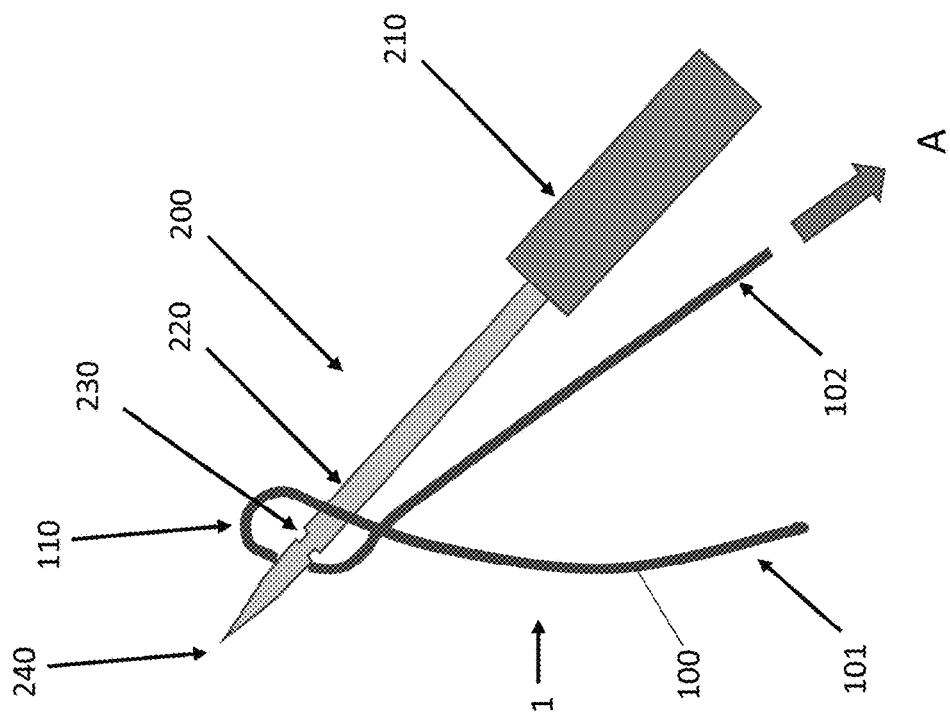

FIGS. 2A and 2B provide for a schematic illustration of how the suture construct 1 can be coupled to, or otherwise associated with, the inserter 200, however other inserters, including but not limited to the curved inserter 700 of FIG. 1C, and other suture constructs that enable features like those provided with respect to construct 1 can be used. As shown in FIG. 2A, the inserter 200 can be passed through the adjustable loop 110 formed by or in the suture filament 100 and, a shown in FIG. 2B, the adjustable loop 110 can be collapsed around the coupling region 230 of the inserter 200. When the reduced diameter section more generally is a feature that may or may not have a reduced diameter, then the adjustable loop 110 can be collapsed around the feature such that it engages the feature to couple the construct 1 to the inserter 200. In the illustrated embodiment, pulling or otherwise applying force to the inside tail 102 of the suture filament in a direction A (FIG. 2A) causes tension in the adjustable loop 110 that reduces a diameter of the loop 110 until the loop 110 becomes engaged with the distal needle 220, as shown at the coupling region 230 of the inserter 200 (FIG. 2B), thereby coupling the construct 1 to the inserter 200. In operation, tension can be held on the inner tail 102 during and after the inserter 200 is introduced into a patient and/or passed through a tissue to be approximated, such actions being described in greater detail below, such as with respect to FIGS. 3A-3L. Holding tension on the inner tail can help, for example, maintain the tension in the adjustable loop 110 and prevent the tissue from dislodging the adjustable loop 110 from the distal needle 220 of the inserter 200. In some embodiments, the coupling feature 230 is configured to allow the adjustable loop 110 of the suture filament 100 to interdigitate with the distal needle 220 of the inserter 200 and maintain the adjustable loop 110 coupled at this location when held in a constricting state, which can allow the user to push or pull the suture filament 100 through tissue.

FIGS. 3A-3L illustrate one exemplary method of use of the suture construct 1 and inserter 200 of FIGS. 1A and 1B, however other inserter designs, such as the curved inserter 700 of FIG. 1C, and other suture constructs can be used. In FIGS. 3A-3L, the inserter 200 is used to pass the suture filament 100 of the construct 1 through a first opening 400 in two pieces of soft tissue 310, 320 and then recapture the suture filament 100 and pull it back out of the two pieces of soft tissue 310, 320 through a second opening 401. The construct 1 is then operated to approximate the two pieces of soft tissue 310, 320 together by collapsing the loop 110 of the filament 100 and maintain the desired location of the tissue 310, 320 by securing the position of the suture filament 100 around the two pieces of soft tissue 310, 320. This example shows the entire process being performed though a single incision 301 in a patient and with only four deliberate movements of the inserter 200 (two insertions and two removals) (more generally this may be referred to as two movements, where the combination of insertion and removal is considered a "single movement"): a first insertion and removal to create the first opening 400 and dispose the suture filament 100 through the two pieces of soft tissue 310, 320, and a second insertion and removal to create the second opening 401 and capture and retrieve the suture filament 100 through the second opening 401.

FIG. 3A is a schematic illustration of the inserter 200 and suture construct 1 in the arrangement of FIG. 2B being introduced to a surgical site in a patient's body though a single incision 301 in the patient's skin 300. The adjustable loop 110 of the suture filament 100 is securely tightened around the distal needle 220 of the inserter so that the adjustable loop 110 is not dislodged during insertion. The sharp tissue-penetrating tip 240 of the inserter 200 can be advanced distally to make the incision 301 or it can be made before introduction of the inserter 200 by the tip 240 or by another tool or instrument. With the sharp tissue-penetrating tip 240 past the incision 301, the sharp tissue-penetrating tip 240 can be advanced distally to be introduced to a soft tissue(s) to be approximated and/or shackled. In FIG. 3A the soft tissue to be approximated is a first piece of soft tissue 310 and a second piece of soft tissue 320, which are shown as being adjacent to each other, under the skin 300, however this is only for ease of illustration. A person skilled in the art will recognize many different tissue configurations with which the described techniques can be applied without departing from the spirit of the present disclosure, and thus the tissue 310, 320 and related portions of the body can represent any number of different tissues and locations in the body. During distal insertion of the sharp tissue-penetrating tip 240 into the body and/or through the tissue 310, 320, tension can be maintained on the inside tail 102 to keep the adjustable loop 110 secured to the distal needle 220 until the adjustable loop 110 is passed completely through the soft tissues 310, 320, as shown in FIG. 3B with both the inside tail 102 and the outside tail 101 of the suture filament 100 now disposed through the soft tissues 310, 320 and extending out of the incision 301. Alternatively, tension need not be applied to the inside tail 102 after the loop 110 has already been collapsed to couple the construct 1 to the inserter 200 while the tissue-penetrating tip 240 is being inserted into the body and/or through the tissue 310, 320. For example, the filament 100 can be engaged with the inserter 200 in such a manner that the loop 110 keeps its collapsed stated during insertion of the inserter 200 into the body.

Figures 3C, 3D:
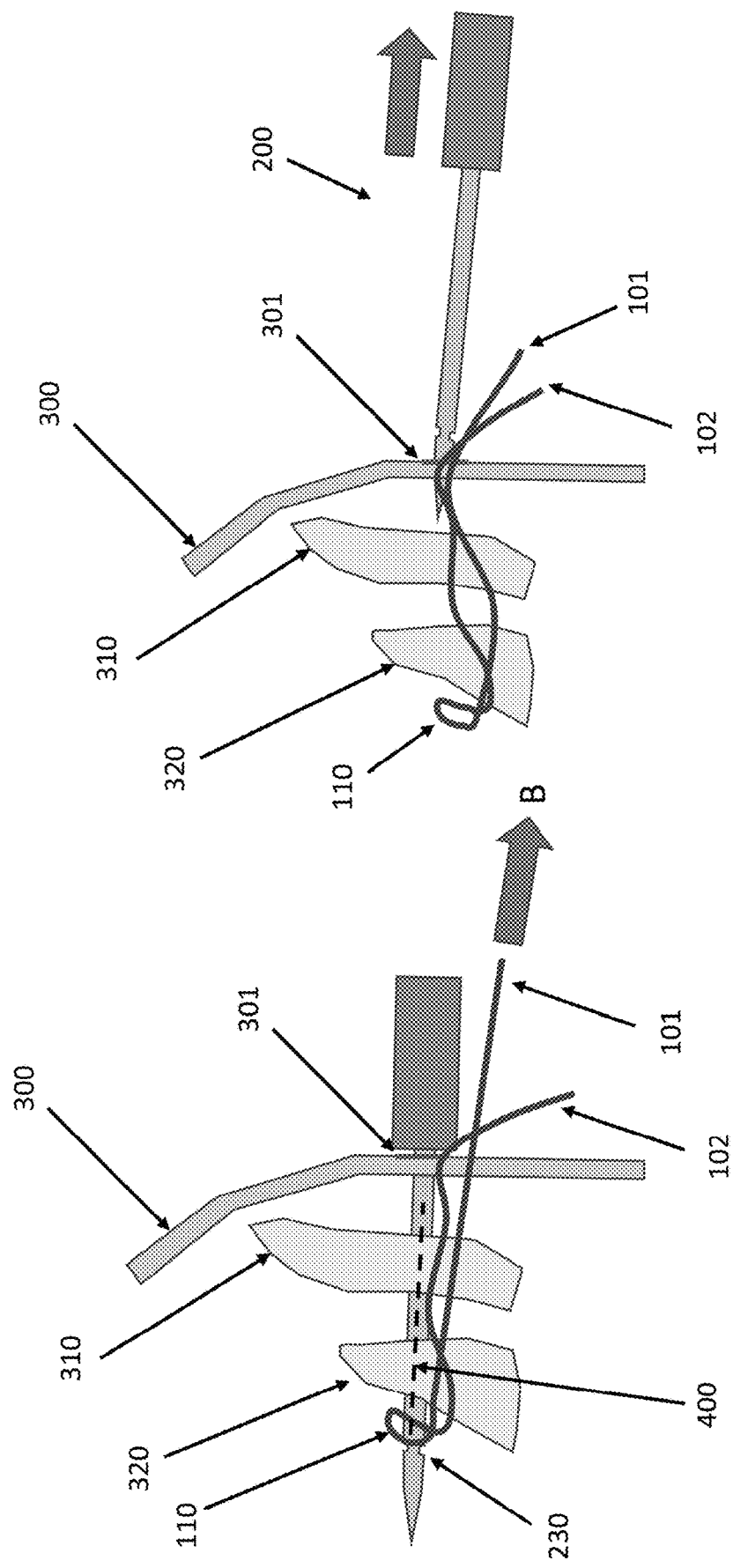

FIG. 3C illustrates how the adjustable loop 110 can be expanded to decouple or otherwise release the suture filament 100 from the inserter 200 after being passed through the soft tissue 310, 320. With the distal needle 220 fully disposing the adjustable loop 110 through a first opening 400 in the soft tissues 310, 320, i.e., the loop 110 has been passed distal of the tissue 310, 320, tension is removed from the inner tail 102 (if it was being applied during and/or after insertion) and then applied to the outer tail 101, as shown by way of a force being applied in a direction B. The surface of the inserter 200 can help to allow the adjustable loop 110 to be expanded in response to the force in the direction B by providing a surface against which the filament 100 can engage to subsequently increase a diameter of the loop 110. The tension on the outer tail 101 expands the adjustable loop 110 and disengages the adjustable loop 110 from the coupling feature 230 of the distal needle 220, as shown in FIG. 3C. With the inner tail 102 free and opposing forces placed in the outer tail 101 and inserter 200, the inner tail 102 feeds back through the opening 109 to enlarge a diameter of the adjustable loop 110, thereby decoupling the suture filament 100 and the inserter 200.

As shown in FIG. 3D, the inserter 200 can be advanced proximally towards the user to remove it from the soft tissue 310, 320, leaving the suture filament 100 disposed through the first opening 400 in the soft tissues 310, 320. Typically the inserter 200 is withdrawn through the same opening it created so as not to create additional trauma to the tissue. With the adjustable loop 110 completely disengaged from the distal needle 220 of the inserter 200, the distal needle 220 is withdrawn from the first opening 400 in the soft tissues 310, 320, leaving the inner tail 102 and the outer tail 101 of the suture filament 100 disposed through the first opening 400 with the adjustable loop 110 at the end of the first opening 400, distal of the soft tissues 310, 320. As illustrated in FIG. 3D, the distal tip 240 can remain in the body to minimize the amount of time the incision 301 has an unrestricted opening formed in it and to reduce the possibility of the inserter 200 forming or being placed in a new opening, thus creating a second incision. Generally it can be desirable to minimize the number of incisions, and open incisions, are formed during a procedure. Further, the inserter 200 may only be withdrawn only through the deep tissue to be fixed by the repair (e.g., the tissue 310, 320), thus allowing the more superficial tissue (e.g., subcutaneous tissue, layers of skin, etc.) to be spared from being captured in the repair. There is no need to retrieve the tails 101, 102 to be tied afterwards because the inserter 200 can be maintained in a singular portal in the superficial tissue throughout the passing steps described herein.

Figures 3E, 3F:
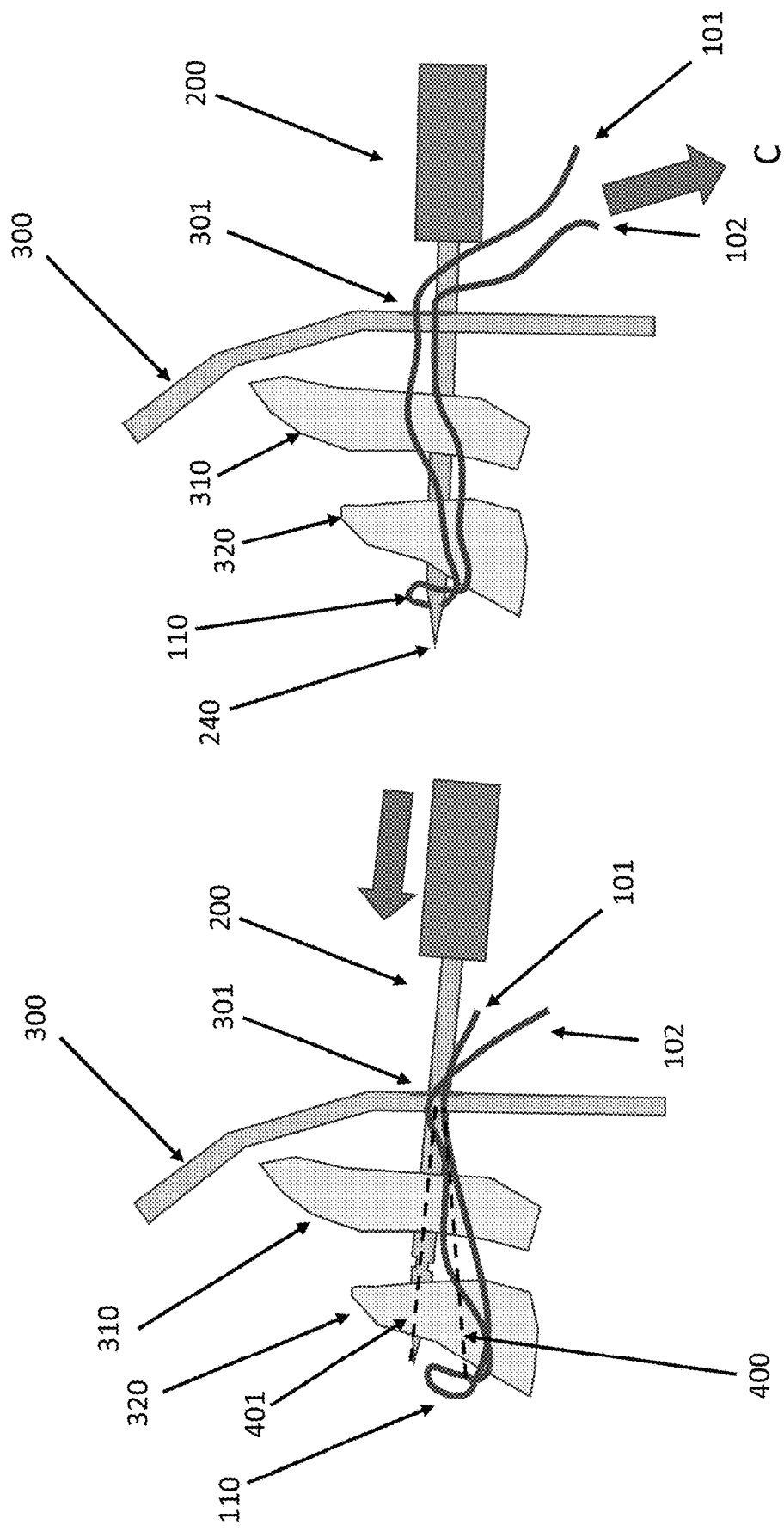

From the position illustrated in FIG. 3D, the sharp tissue-penetrating tip 240 can be reinserted though the soft tissues 310, 320 at a new location, forming a second opening 401, as shown in FIG. 3E. More particularly, FIG. 3E shows the inserter 200 being passed through a second location 401 in the soft tissues 310, 320. With the inserter 200 having been completely decoupled from the suture filament 100, the reinsertion of the distal needle 220 through the soft tissues 310, 320 at the second location 401 does not disrupt the inner tail 102, the outer tail 101, or the adjustable loop 110. The sharp tissue-penetrating tip can be navigated through the expanded adjustable loop 110, as shown in FIG. 3F, for subsequent re-attachment of the adjustable loop 110 to the inserter 200. In operation, the sharp tissue-penetrating tip 240 of the inserter 200 is driven or otherwise passed through the adjustable loop 110 after being passed through the second opening 401 due to the second opening 401 being in close-enough proximity to the first opening 400 to permit the adjustable loop 110 to be within reach of the sharp tissue-penetrating tip 240 when the distal needle 220 is disposed through the second opening 401. Various visualization techniques known to those skilled in the art can be used to help identify the location of the adjustable loop 110. These can include a scope (e.g., endoscope, laparoscope, etc.), diagnostic ultrasound, or terahertz visualization, among other techniques. Alternatively, or additionally, the loop 110 and/or the filament 100 more generally can include one or more identifiers on it to help identify its location within the body with or without visualization. By way of non-limiting example, the loop portion can have some sort of tactile feedback disposed on it (e.g., a material or coating different than the suture filament, a raised shape formed on the loop 110, etc.) to help assist in identifying its location when disposed in the body.

Thereafter, as shown in FIG. 3F, a force in the direction C can be applied to the inside tail 102, thereby creating tension that can shrink the diameter of the adjustable loop 220 around the distal needle 220. The distal needle 220 can be adjusted as necessary to ensure that the adjustable loop 110 is coupled to the coupling region 230 of the distal needle 220. In some instances, the location of the coupling region 230, as shown a reduced diameter section, is close to the sharp tissue-penetrating tip 240 such that the adjustable loop 110 is shrunk around the distal needle 220 proximal to the reduced diameter section 230 and a subsequent withdrawal of the inserter 200 from the second opening 401 and tension in the inner tail 102 causes the adjustable loop 110 to move distally along the distal needle 220 until the adjustable loop 110 engages with the reduced diameter section 230, after which continued withdrawal of the inserter 200 from the second opening 401 draws the adjustable loop 110 through the second opening 401 along with lengths of the inner tail 102 and outer tail 101, as shown in FIG. 3G.

Figure 3G:
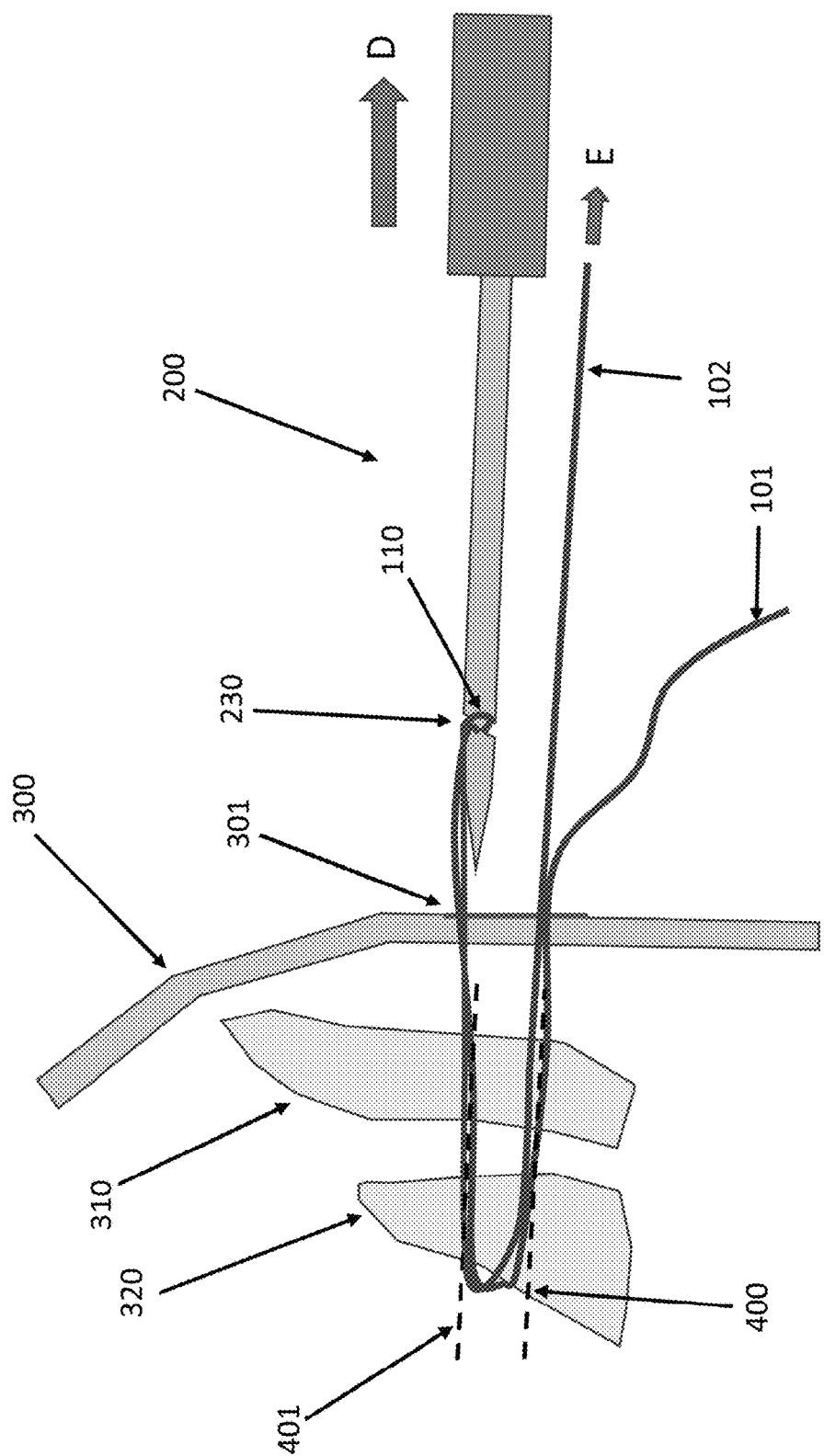

FIG. 3G more particularly illustrates distal withdrawal of a portion of the filament 100, as shown the collapsible loop 110, from the surgical site. As shown the inserter 200 can be withdrawn from the second location 401 in the soft tissues 310, 320 and the incision 301 with the adjustable loop 110 in a direction D such that the inner and outer tails 102, 101 are passed through both the first and second locations 400, 401 in the soft tissues 310, 320 and back out through the incision 301. Tension can be maintained on the inner tail 102, as shown by applying a force to the inner tail 102 in a direction E, as the inserter 200 is withdrawn proximally to ensure that the adjustable loop 110 is retained by the coupling feature 230 to retrieve the adjustable loop 110 from the soft tissues 310, 320 and, at least in some embodiments, bring the adjustable loop 110 past the incision 301. Similar to previous instances related to movement of the inserter 200 and filament 100 simultaneously, in some instances the formation of the couple between the filament 100 and the inserter 200 can be such that no tension application is used while removing the inserter 200 and the filament 100 from the surgical site.

Figure 3H:
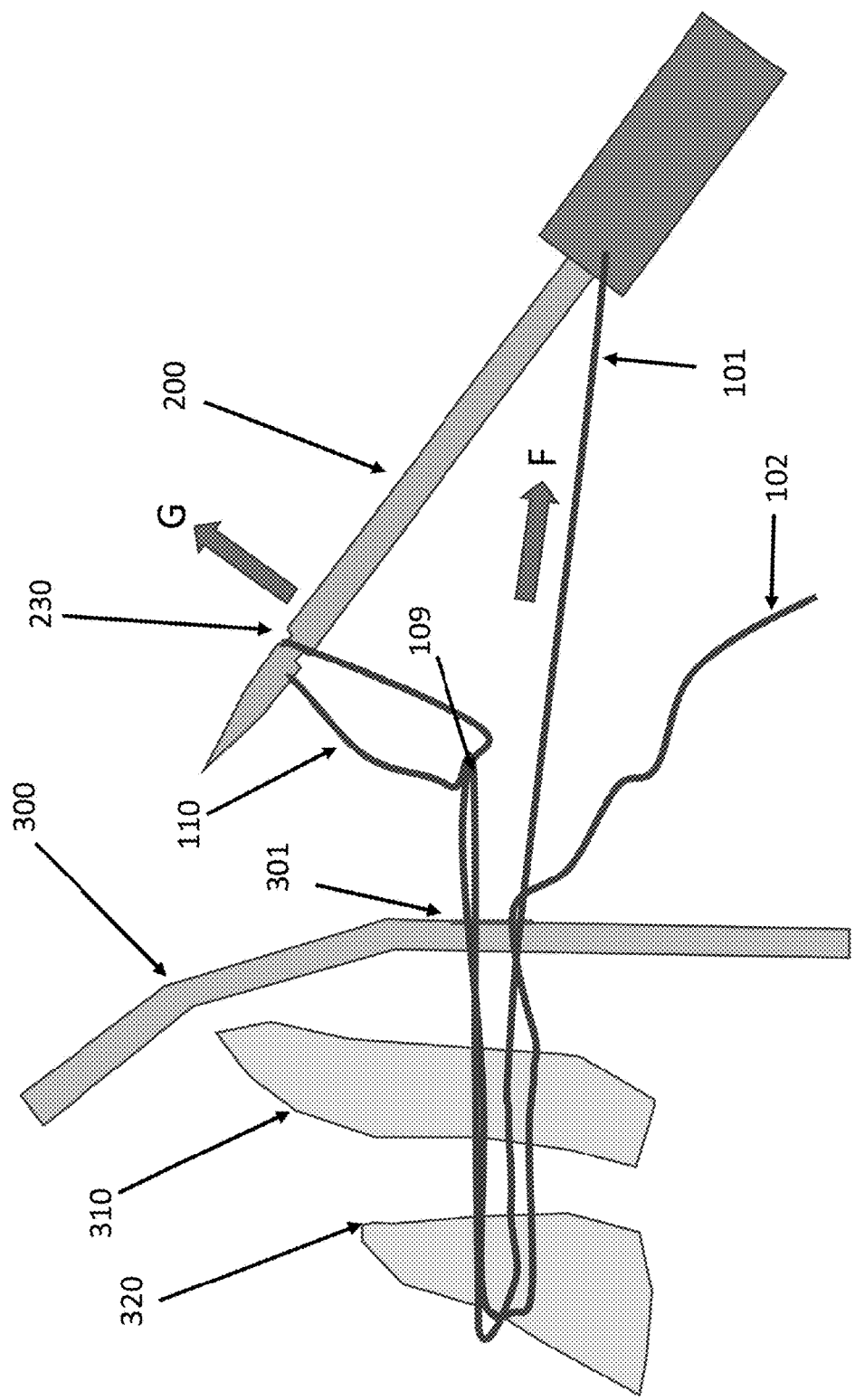
Figure 31:
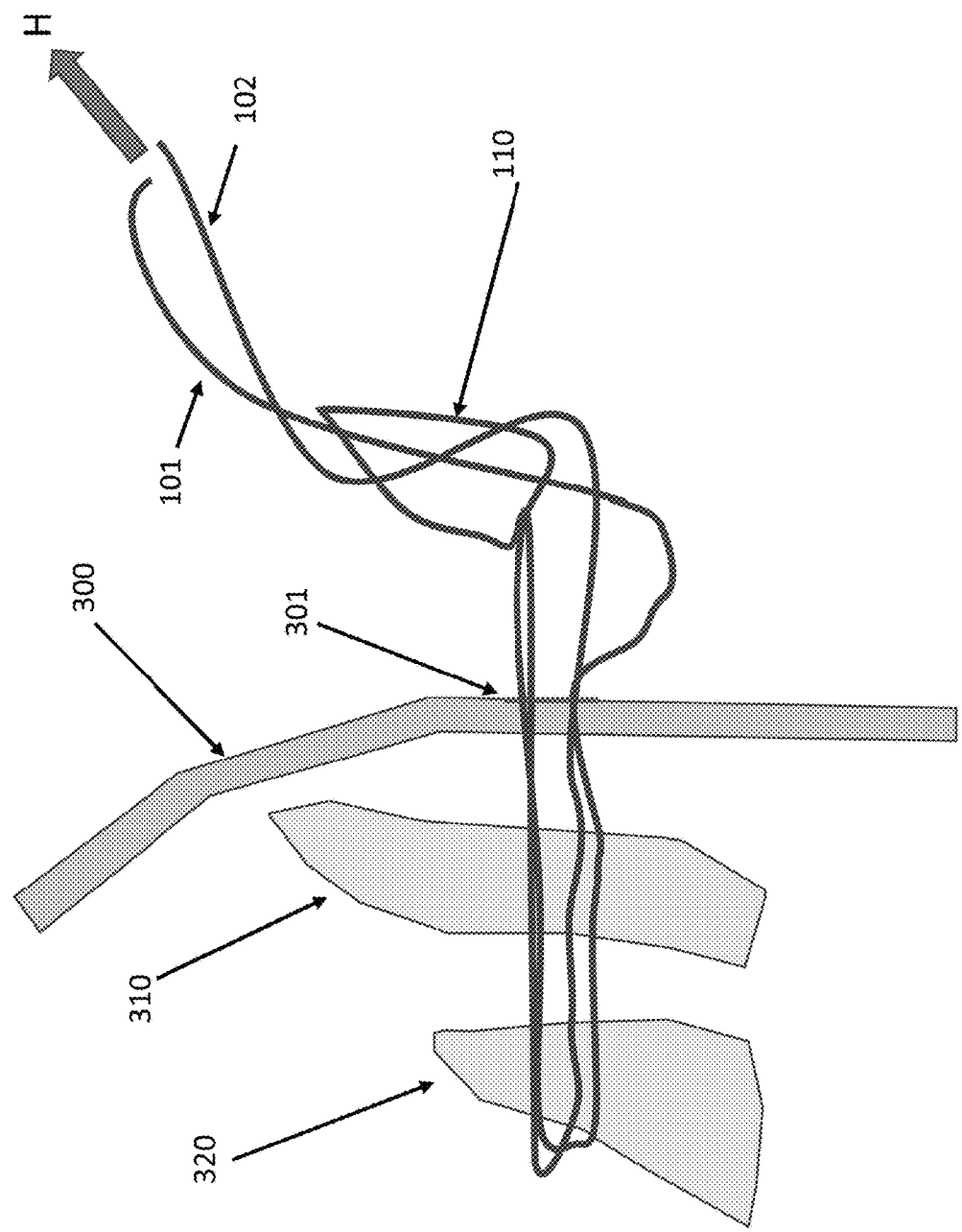

FIG. 3H provides for a second instance in which the diameter of the adjustable loop 110 is expanded to decouple the filament 100 from the inserter 220. As in the previous instance, this can be achieved by applying a force to the outside tail 101, as shown in a direction F, thereby applying tension to the outside tail 101. This can be done, for example, after the inserter 200 and adjustable loop 110 have been completely withdrawn from the patient's body. A person skilled in the art will appreciate that at least because the decoupling of the filament 100 from the inserter 220 is occurring outside of the body, there are many different actions that can be performed to disassociate the filament 100 from the inserter 220, and such actions are suitable alternatives, or additional actions, to applying a force to the outside tail 101. With the adjustable loop 110 free from the body and/or the soft tissues 310, 320, tension can be removed from the inner tail 102 and then applied to the outer tail 101 while holding the inserter 200 to expand the adjustable loop 110 and disengage the adjustable loop 110 from the inserter, as shown in FIG. 3H. The surface of the inserter 200 can help to allow the adjustable loop 110 to be expanded in response to the force in the direction F by providing a surface against which the filament 100 can engage to subsequently increase a diameter of the loop 110.

In fact, the inserter 200 can apply a force to the loop 110 by being moved in a direction G in lieu of or in addition to the force F to increase the diameter of the loop 100. In operation, this is similar to the release of the adjustable loop 110 that previously occurred inside the patient, however, here the release may be done more dramatically to create a large loop for easy of threading the suture tails in the subsequent steps due, at least in part, to there being more room to perform the loop expansion.

FIG. 3I is a schematic illustration of an exemplary embodiment of a luggage tag knot being tied in the suture filament 110 by passing the inner tail 102 and outer tail 101 through the adjustable loop 110 after the adjustable loop 110 has been expanded and disengaged from the inserter 200. In operation, a user may now grab the inner tail 102 and outer tail 101 and pass them through the adjustable loop 110 and then pull them to complete the luggage tag knot. As the tails 102, 101 are passed through the loop 110 and a force in a direction H is applied to one of the tails, e.g., the inner tail 102, eventually a diameter of the loop 110 will decrease, causing the loop 110 to collapse on the tails 101, 102.

As the force H is continued to be applied to the inner tail 102, the collapsed loop 110 advances back through the incision 301 to approximate the soft tissues 310, 320. The collapsed loop 110 itself forms a snare 120 having a loop or loop portion 122, the loop 122 being disposed in and around the tissues 310, 320. By applying tension to the inner tail 102 to shrink the loop 122 in and around the soft tissue as shown in FIGS. 3J and 3K, the tissues 310, 320 are drawn together. Tensioning the inner tail first can insure the luggage knot is appropriately dressed by forcing the loop of the luggage knot to collapse to the diameter of the tails 101, 102 threaded through it before the shackle loop length of the luggage knot is defined by the captured tissues 310, 320. Tensioning with the outer tail 101 first may reduce the knot strength if the loop of the luggage knot defines a portion of the circumference of the shackle and subsequent adjustment with the inner tail 102 may not reduce the luggage knot as intended.

Figure 3L:
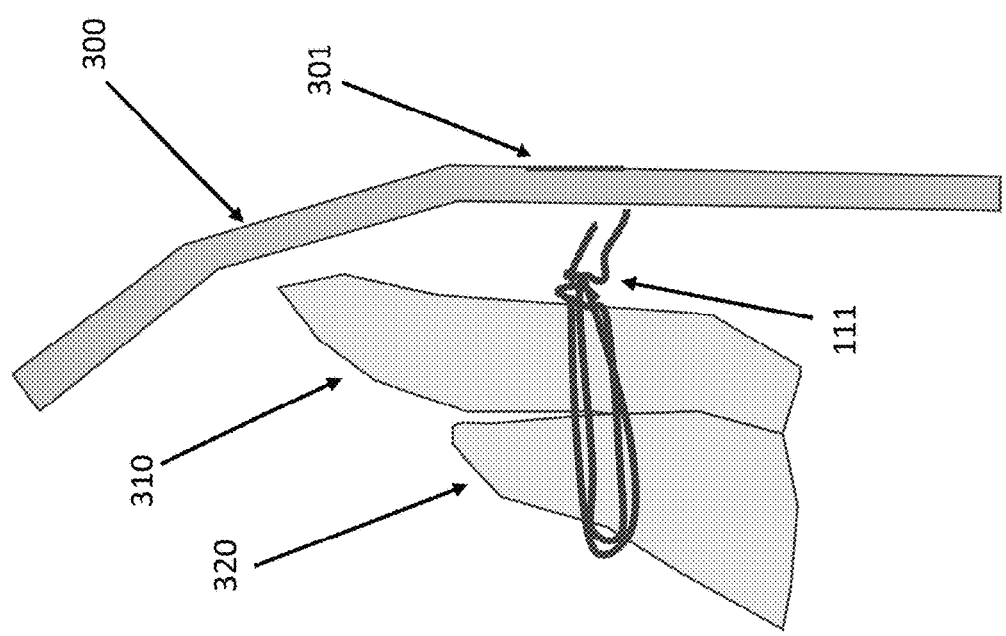

As shown in FIG. 3L, after the filament 100 and tissue 310, 320 have been adjusted to desired positions and locations, one or more half hitch knots 111 can be tied or otherwise formed, such as by using the inner limb 102 as the post, for final tension and security. Such knot(s) 111 can maintain the location of the filament 100, helping to cause the knot to be properly dressed, and reduce the possibility of knot and/or suture slippage that may cause the filament 100 to undesirably loosen. Further, the inner tail 102 and outer tail 101 can be trimmed so they remain inside the skin incision 301, thereby enabling closure of the incision 301 and minimizing the amount of material disposed in the body that may cause unintended trauma to tissue or the like. The tails 101, 102 can be trimmed using any number of techniques known to those skilled in the art, including but not limited to using with an arthroscopic suture cutter.

FIGS. 4 and 5 illustrate example geometries of the reduced diameter portion 230 of the inserter 200. The transition of the reduced diameter or geometry of the distal needle 240 of the inserter 200 may take a form to require less tension in the inner tail 102 to maintain the coupling of the adjustable loop 110 to the distal needle 220. Conversely, the geometry may be such that the adjustable loop 110 will release easier. FIG. 4 illustrates one example that be used to reduce the resistance of disengaging the adjustable loop 110 from the distal needle 220 by forming the reduced diameter section 230 with one or more chamfered edges 231 to create an inclined transition between the reduced diameter section 230 and the distal needle 220 to facilitate easier release of the adjustable loop 110. Alternatively, or additionally, FIG. 5 shows one example that can be used for increasing the amount of interdigitation between the adjustable loop 110 and the distal needle 220, increasing a depth of the reduced diameter section 230 relative to a thickness of the suture filament 100, to increase the retention ability of the transition 232 between the reduced diameter section 230 and the distal needle 220. In some examples, a combination of both examples of FIGS. 4 and 5 is possible, with differencing proximal and distal transition geometries about the reduced diameter section. In some example, the transition and/or the size and shape of the reduced diameter section can vary circumferentially around the distal needle 220.

Figure 6:
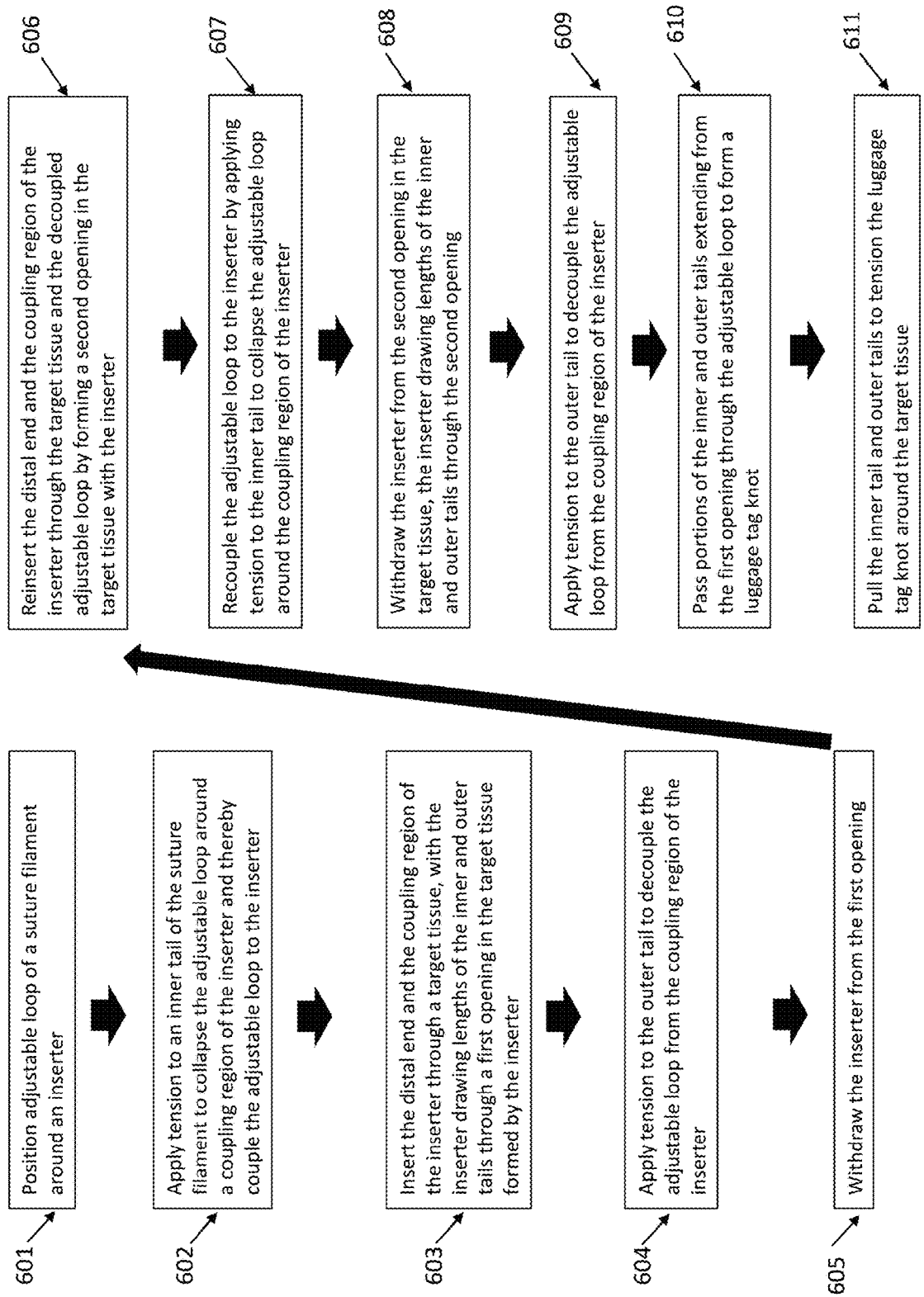
FIG. 6 is a flowchart of one exemplary embodiment of a minimally invasive method for approximating tissue through a single incision using an inserter and a suture filament having an adjustable loop, like the insert and suture filament of FIGS. 1A and 1B.

FIG. 6 provides a flowchart of an exemplary embodiment of a minimally invasive method for approximating tissue 310, 320 through a single incision 301 using an inserter 200 and a suture filament 100 having an adjustable loop 110 formed by passing an inner tail 102 through an outer tail 101. In a first step or action (these words may be used interchangeably) 601, the adjustable loop 110 of a suture filament is positioned around a distal end of an inserter 200. Next, in step 602, tension can be applied to an inner tail 102 of the suture filament 100 to collapse the adjustable loop 110 around a coupling region 230 of the inserter 200 (e.g., a reduced diameter portion, although other configurations for this region are possible) and thereby couple the adjustable loop 110 to the inserter 200. Once coupled, in step 603, the distal end 240 of the inserter and the coupling region 230 can be inserted into target tissues 310, 320 to be approximated or reduced, with the inserter 200 drawing lengths of the inner and outer tails 101, 102 through a first opening 400 in the target tissue 310, 320 formed by the inserter 200.

With the inserter 200 disposed in the target tissue until the adjustable loop 110 is passed therethrough, tension can be applied to the outer tail 101 in step 604 to decouple the adjustable loop 110 from the coupling region 230 of the inserter and, in step 605, the inserter 200 can be removed from the target tissue 310, 320 without the suture filament 100. In step 606, the inserter 200 can be reinserted though the target tissue 310, 320 at a second location, forming a second opening 401, and the distal end of the inserter 200 can be passed through the open adjustable loop 110 that was left in the target tissue 310, 320. In step 607, tension can be applied to the inner tail 102 to recouple the adjustable loop 110 around the inserter 220 at the coupling region 230 and, in step 608, the inserter with the adjustable loop 110 coupled thereto can be withdrawn from the second opening 401, which can draw the inner tail 102 and outer tail 101 through the second opening 401 as well as further through the first opening 400. In step 609, with the inserter and adjustable loop 110 removed from the target tissue 310, 320 tension can be applied to the outer tail 101 to decouple the adjustable loop 110 from the inserter. At step 610 the inner tail 102 and outer tail 101 can be passed through the adjustable loop 110 to form a luggage tag knot and loop around the target tissue 310, 320 through the first and second openings 400, 401. Finally, at the 611, the resulting luggage tag knot can be collapsed distally towards and to the surgical site, by applying tension to one of the inner and outer tails 102, 101, drawing the target tissue 310, 320 together. The location of the luggage tag knot with respect to the tissues 310, 320 can be set and one or more half-hitch knots can be formed to secure that location. The tails 101, 102 can be trimmed and the incision 301 closed to complete the operation.

While the FIGS. 1A-3L have shown the suture filament 100 as a single strand, other configurations are contemplated, and one skilled in the art would appreciate that a number of suture constructs having an adjustable loop are able to be used according to the disclosures herein. Additionally, while the inserter 200 has been shown as having a generally elongate shape with a distal needle and proximal handle, other sizes, shapes, and arrangements are contemplated to enable the insertion and removal steps disclosed herein. For example, the inserter 200 could be part of a larger tool assembly, such as that is operated by a robot or other surgical-assistance system. Similarly, while the coupling region 230 of the inserter 200 has been shown as a reduced diameter section, other arrangements are contemplated, such as automated features or structures of the inserter 200 that selectively assist in the coupling and/or decoupling of the adjustable loop 110 to the inserter.

As noted above, any of a variety of surgical procedures can be performed utilizing the suture filament and inserter embodiments described herein. For example, two procedures that can benefit from the present disclosure is meniscal repair and soft tenodesis of the long head of the biceps. Other exemplary procedures can include any procedure throughout the body requiring fastening a suture through soft tissue, including various orthopedic procedures throughout the body, including various joint, ligament, and tendon repairs.

Figure 7A:
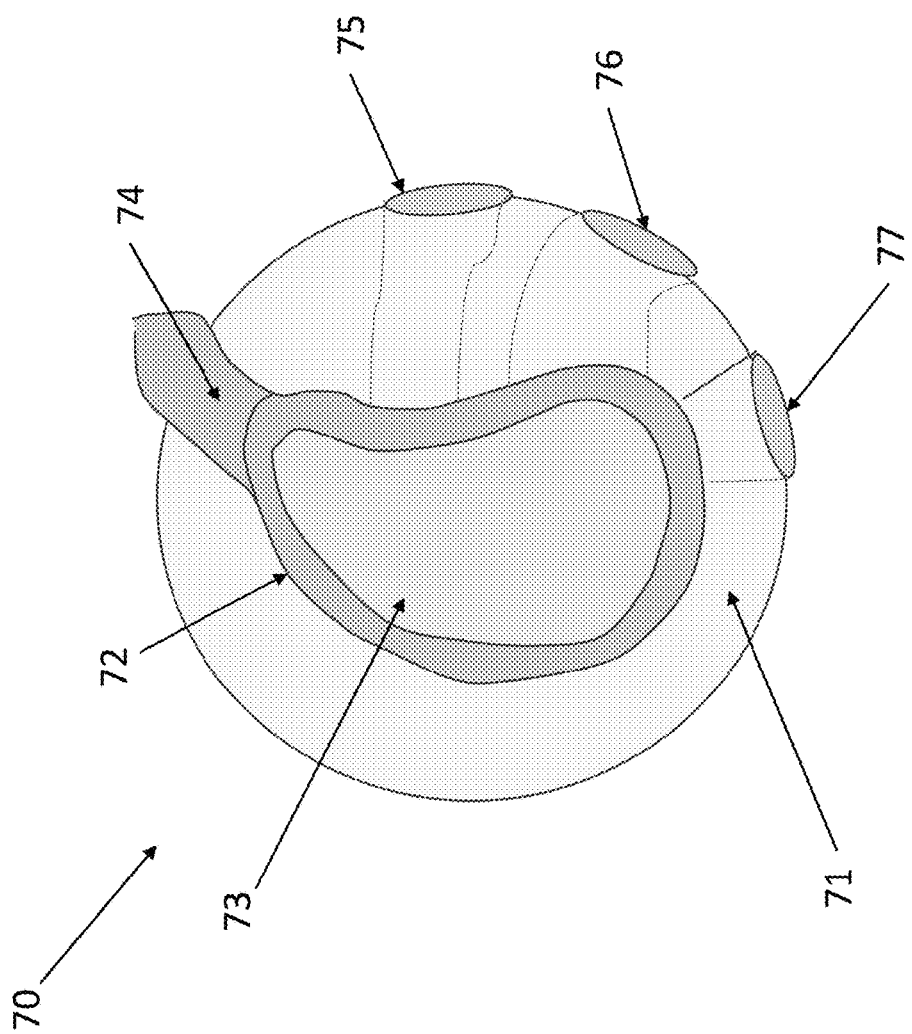
FIGS. 7A-7H provide for a schematic illustration of one exemplary embodiment of a surgical procedure using the suture filament of FIG. 1A and the inserter of FIG. 1C.

FIGS. 7A-7H show embodiments of an example surgical application of the present disclosure using the curved inserter 700. Specifically, FIGS. 7A-7H show a multidirectional shoulder instability being treated by a capsule plication operation conducted using aspects of the present disclosure. FIG. 7A illustrates a shoulder region 70 of a patient, including the joint capsule 71, labrum 72, glenoid 73, biceps tendon 74, superior glenohumeral ligament 75, middle glenohumeral ligament 76, and inferior glenohumeral ligament 77.

Figure 7B:
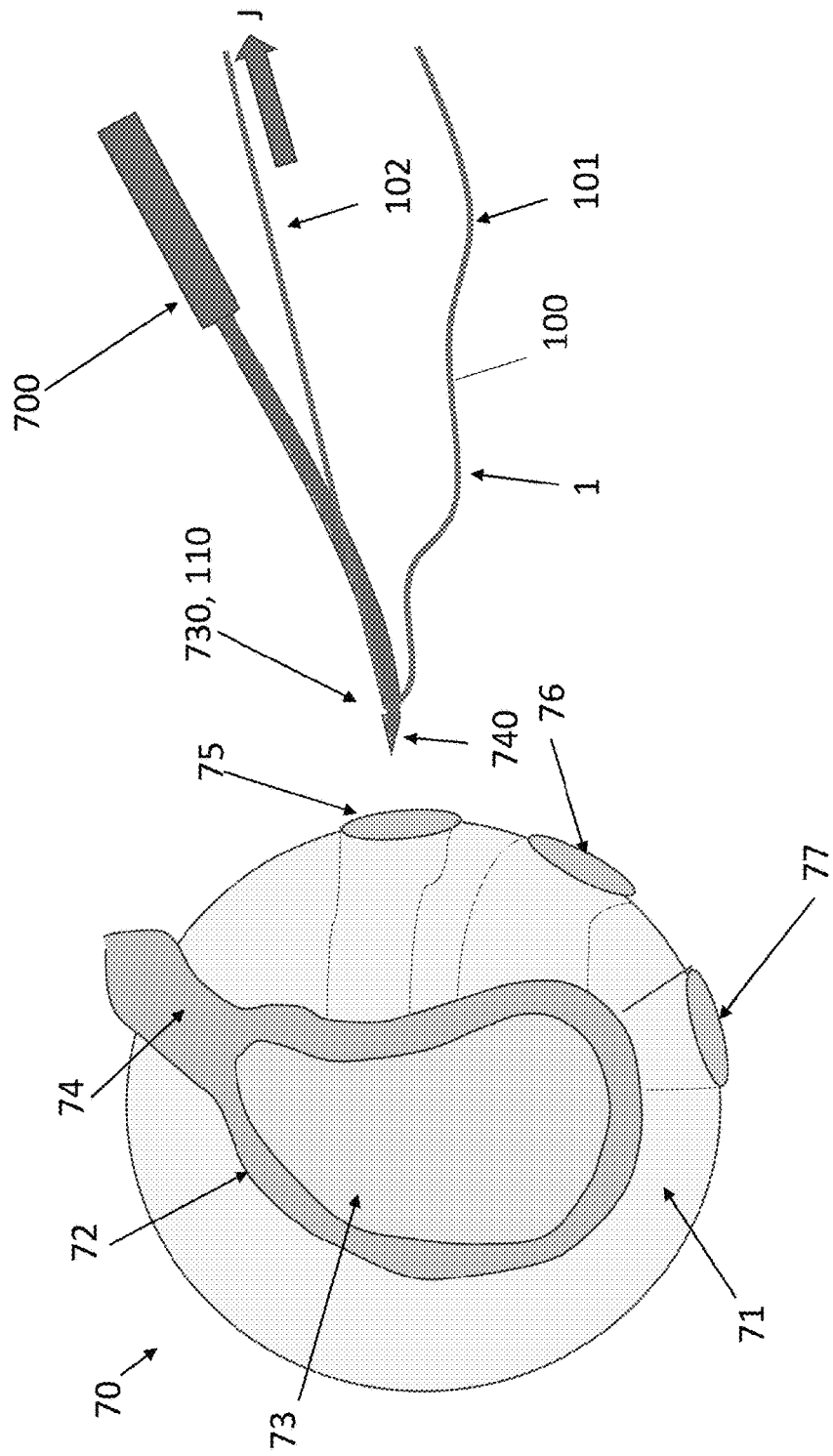
Figure 7C:
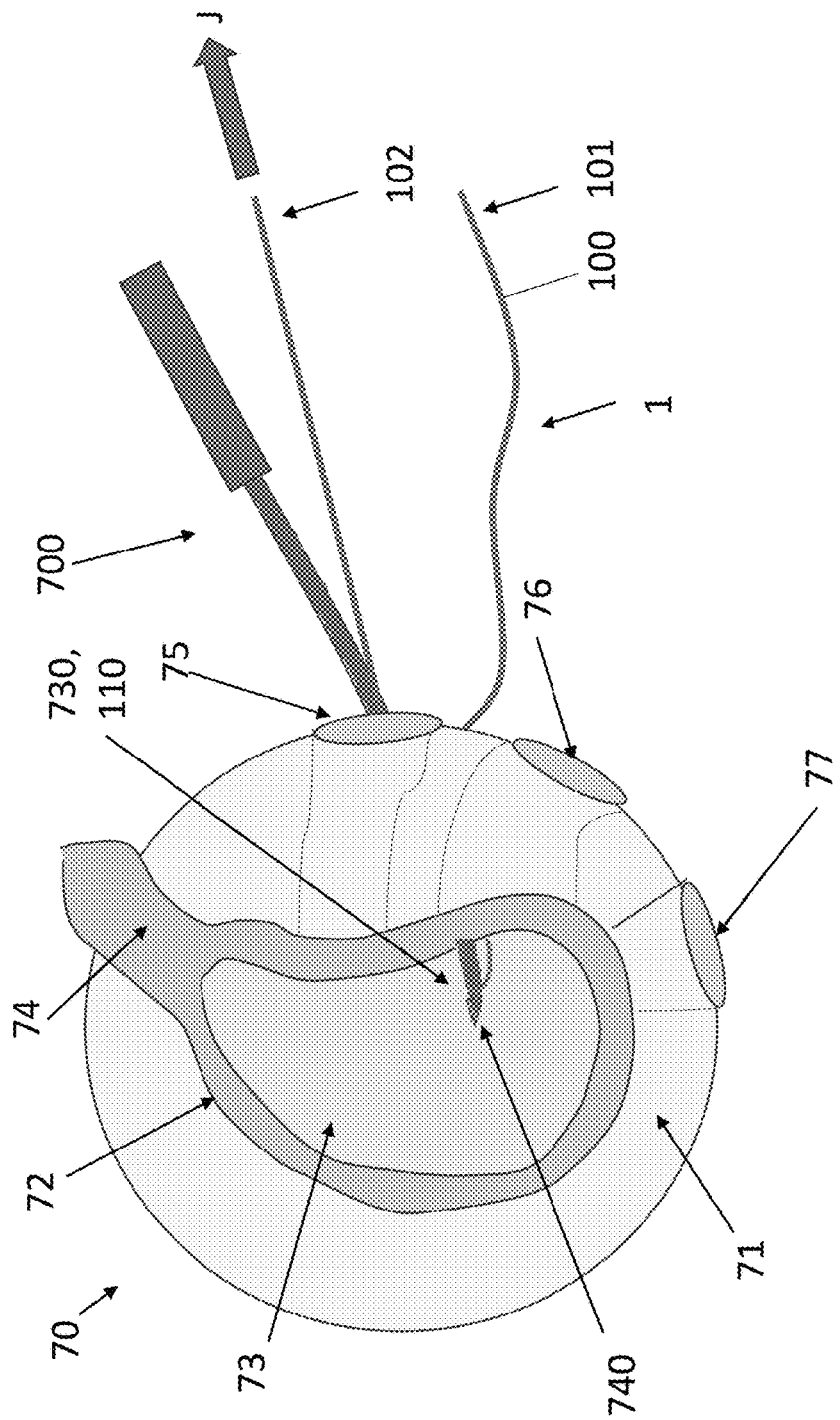
Figure 7D:
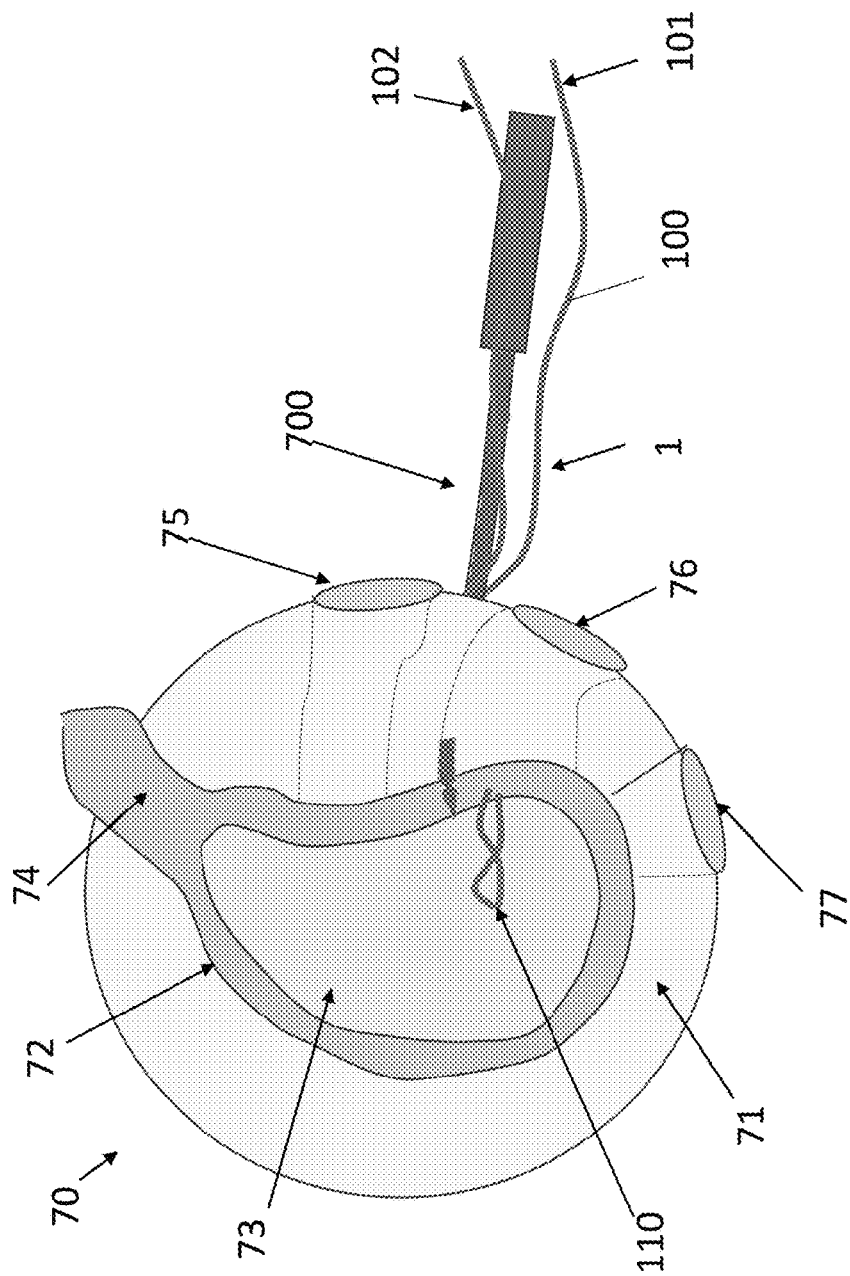
Figure 7E:
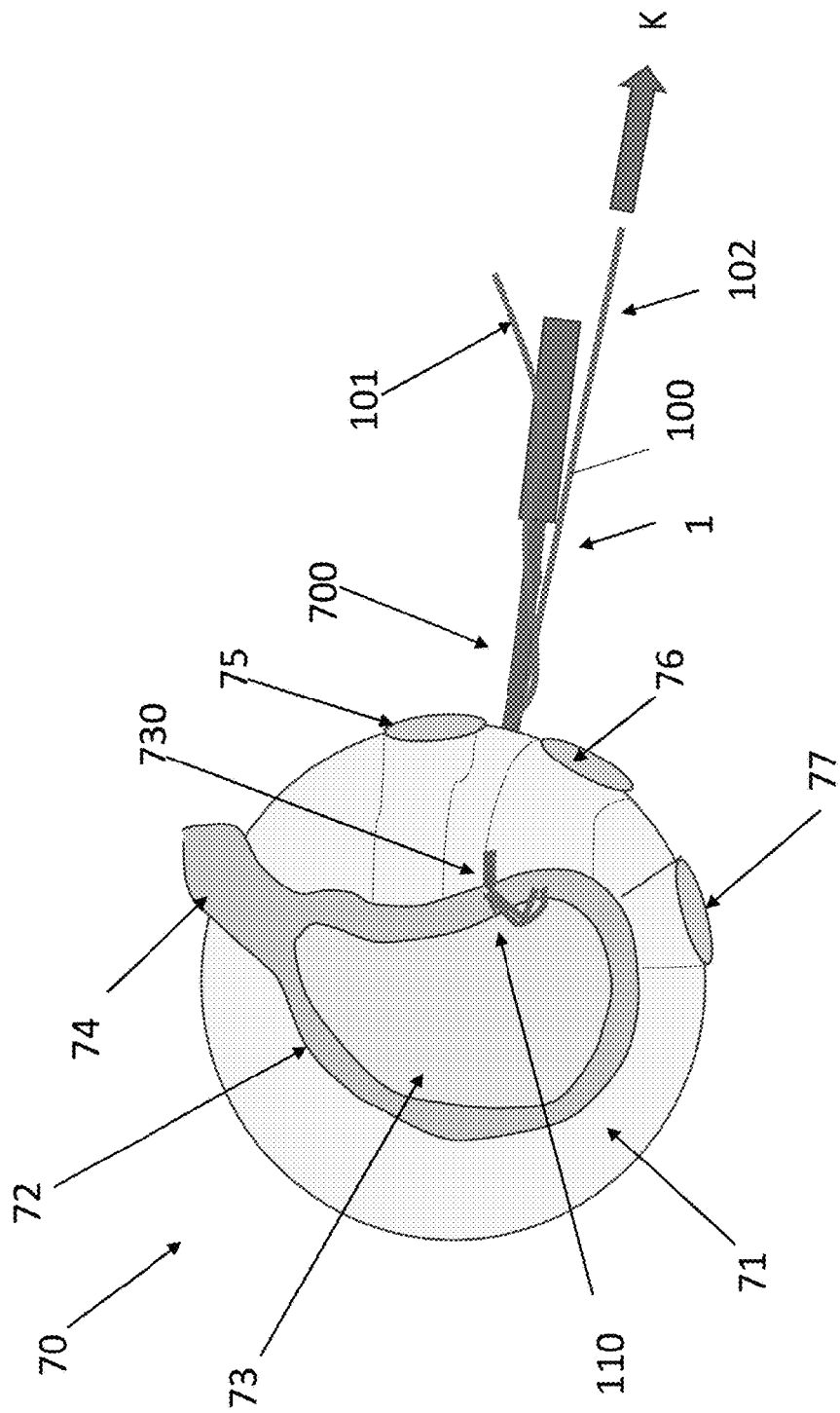

In FIG. 7B, a construct 1 is coupled with the curved inserter 700 such that the adjustable loop 110 is tightened to and secured around the reduced diameter section 730 of the curved inserter 700 by applying a force J onto the inner tail 102 of the suture filament 100. Next, while holding the tension force J on the inner tail 102, the sharp tissue-penetrating tip 740 penetrates the joint capsule 71 and into labrum 72 at a first location, as shown in FIG. 7C. Once the sharp tissue-penetrating tip 740 has reached a desired depth/ location, the adjustable loop 110 is decoupled from the reduced diameter section 730 of the distal needle 720 of the curved inserter, for instance by applying a force (not shown) onto the outer tail 101 of the suture filament 100, and the curved inserter 700 is subsequently retracted from the first location, as shown in FIG. 7D. After the sharp tissue-penetrating tip 740 is retracted from the tissue layers to be incorporated into the repair, as shown in FIG. 7E, the sharp tissue-penetrating tip 740 is reinserted at a second location, thereby taking a bite of tissue between the first location (where the suture filament 100 is now disposed) and the second location (where the distal needle 720 of the curved inserter is now disposed). With the sharp tissue-penetrating tip 740 having passed through the second location, the sharp tissue-penetrating tip 740 is navigated through the adjustable loop 110 and a tensioning force K on the inner tail 102 constricts the adjustable loop around the reduced diameter section 730, as also shown in FIG. 7E.

Figure 7F:
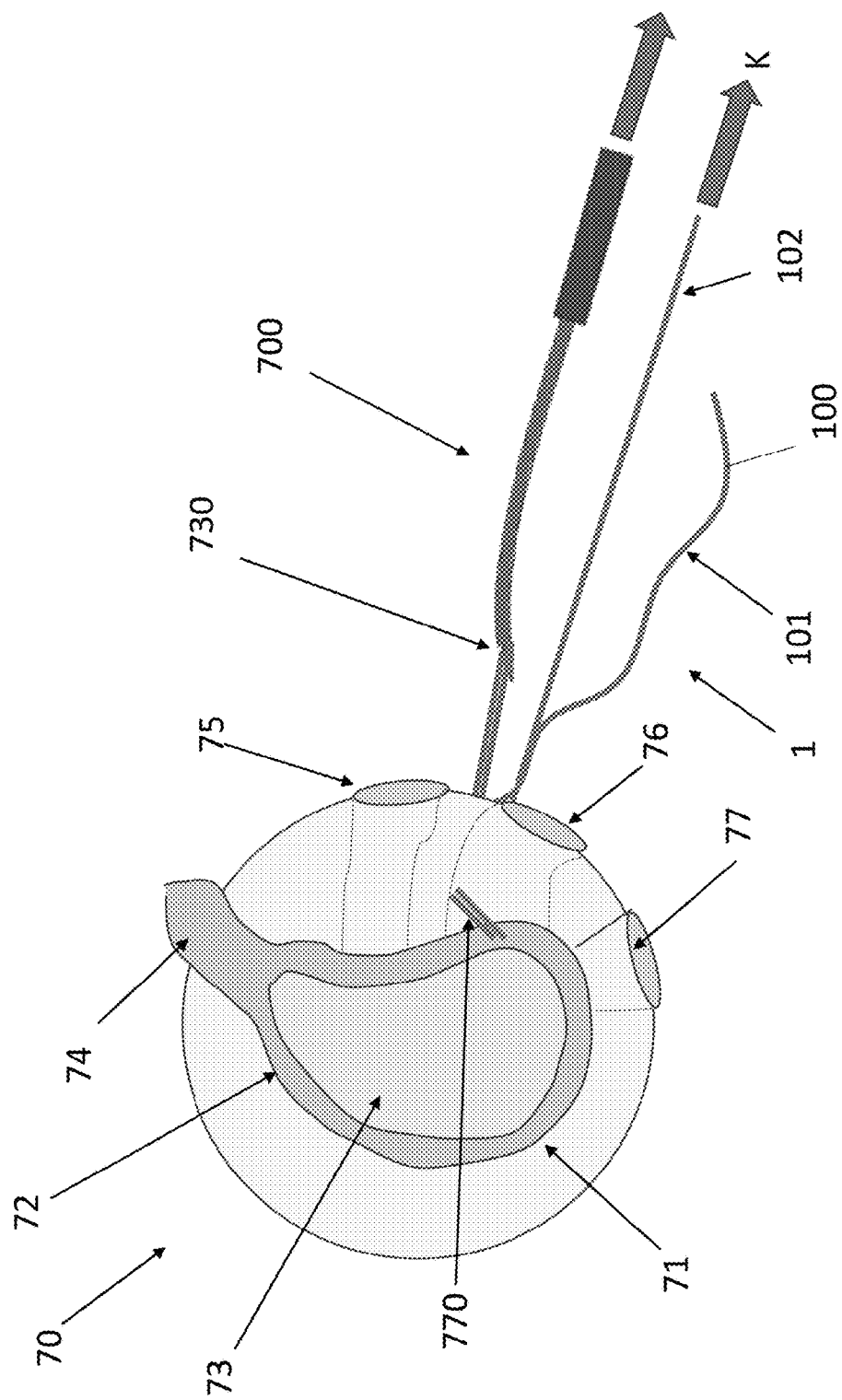
Figure 7G:
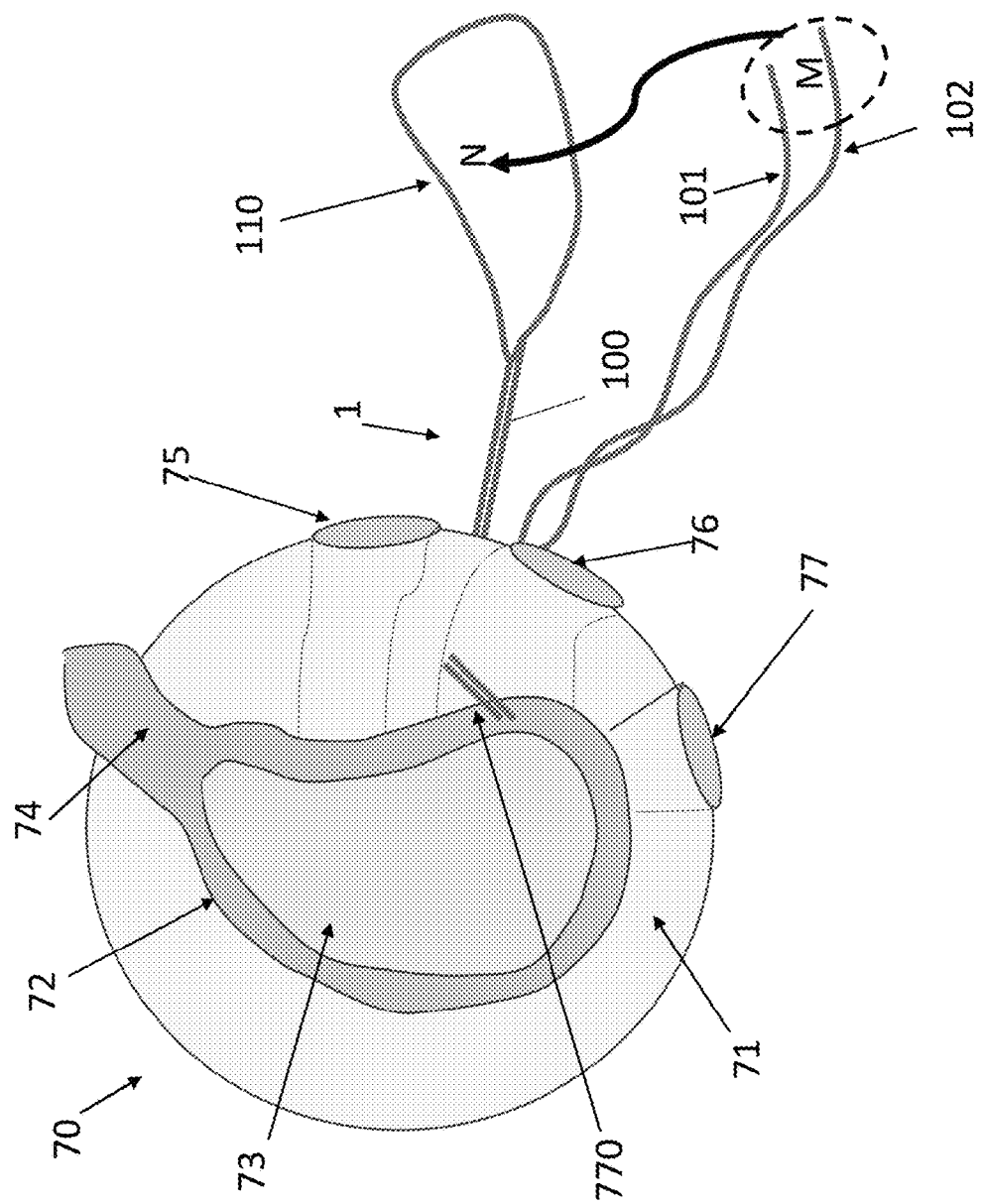

Once the curved inserter 700 has been recoupled with the suture filament 100, continued tension force K can be held on the inner tail 102 to maintain the coupling of the suture filament 100 and curved inserter 700 and the curved inserter 700 is retracted to retrieve the adjustable loop 110 of the suture filament 100 from the patient through the second location, as shown in FIG. 7F. FIG. 7F also shows the repair location 770 of the suture filament 110 in the soft tissue between the first and second locations, with this location 770 being the location to be approximated by tightening of the construct in a final step to be described below. With the adjustable loop 110 removed from the patient, a tensioning force can be applied to the outer tail 101 to decouple the adjustable loop 110 from the reduced diameter 730 section of the curved inserter 700 and the adjustable loop 110 can be expanded. FIG. 7G shows the curved inserter 700 removed from the construct 1, and the ends M of the inner and outer tails 102, 101 can be threaded through the open adjustable loop 110 (as indicated by path N of the ends M) to complete a luggage tag knot with the construct 1. Subsequently, the luggage tag knot formed by the construct 1 can be reduced around the repair location 770 by pulling on the inner tail 102 first to ensure the knot is properly dressed with respect to the outer tail 101. Next, the first and second locations (spanned on an inside side of the soft tissue at the repair location 770) are approximated by reducing the construct's 1 size around the soft tissue, for instance by applying tension to at least one of the inner and outer tails 102, 101. Additionally, as detailed above, a half hitch can be tied using the inner tail 102 as the post to lock the construct in the knotted configuration with the tissue held in the approximated arrangement. Notably, although not described with as much specificity, the techniques, repairs, and systems described herein can be applied to the repair illustrated in FIGS. 7A-7H, and likewise, the techniques and systems described with respect to FIGS. 7A-7H can be applied to the techniques, repairs, and systems described throughout the present disclosure.

Figure 7H:
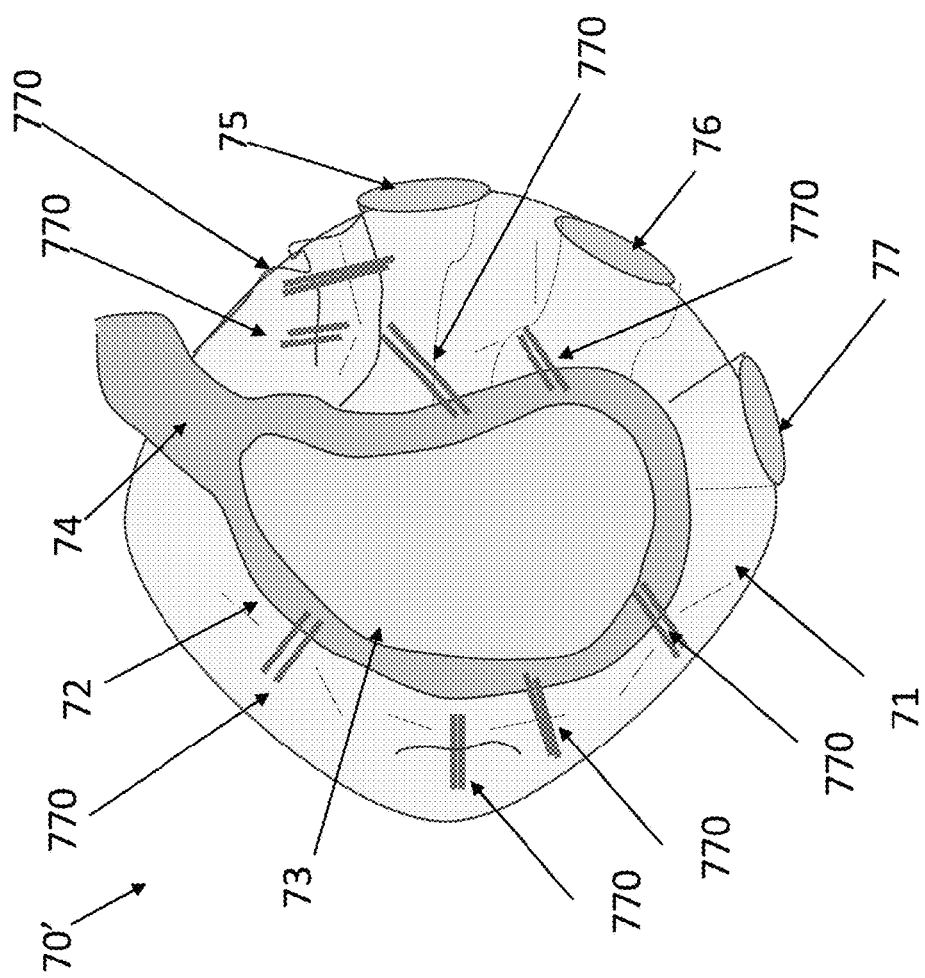

In the operation of addressing a multidirectional shoulder instability, the steps of FIGS. 7B-7G can be repeated at multiple repair locations 770s around the soft tissue in the should region 70 in order to create a stabilized shoulder region 70' as shown in FIG. 7H.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments, devices, and systems disclosed herein can be constructed from any of a variety of known materials. Exemplary materials for the inserters 200, 700 include those which are suitable for use in surgical applications, including metals such as stainless steel, titanium, nickel, cobalt-chromium, or alloys and combinations thereof, polymers such as PEEK, ceramics, carbon fiber, and so forth. The various components of the inserters 200, 700 disclosed herein can have varying degrees of rigidity or flexibility, as appropriate for their use. Inserter 200,700 sizes can also vary greatly, depending on the intended use and surgical site anatomy. Furthermore, particular components can be formed from a different material than other components. One or more components or portions of the inserters 200, 700 and or construct 1 can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The constructs 1 and suture filaments 100 can include an elongate suture filament, and a variety of different types of suture filaments can be used, including but not limited to a cannulated filament, a braided filament, and a mono filament, and such filaments can be, for example, absorbable, nonabsorbable, and swellable. The type, size, and strength of the filament can depend, at least in part, on the other materials of the construct 1 and the tissue, bone, and related tunnels through which it will be passed, and the type of procedure in which it is used.

In one exemplary embodiment the suture filament is a #0 filament (about 26 gauge to about 27 gauge), such as an Orthocord™ filament that is commercially available from DePuy Synthes Sports Medicine (Mitek), 325 Paramount Drive, Raynham, Massachusetts 02767, or an Ethibond™ filament that is commercially available from Ethicon, Inc., Route 22 West, Somerville, NJ 08876. In another exemplary embodiment the suture filament has a solid core and is swellable, such as DePuy Synthes Dynacord™ suture, also available from DePuy Synthes Sports Medicine (Mitek) of Raynham, MA The thickness of the filament should provide strength in the connection but at the same time minimize the trauma caused to tissue through which it passes. In some embodiments the suture filament can have a size in the range of about a #5 filament (about 20 gauge to about 21 gauge) to about a #3-0 filament (about 29 gauge to about 32 gauge). Orthocord™ suture is approximately fifty-five to sixty-five percent PDS™ polydioxanone, which is bioabsorbable, and the remaining thirty-five to forty-five percent ultra-high molecular weight polyethylene, while Ethibond™ suture is primarily high strength polyester. The amount and type of bioabsorbable material, if any, utilized in the suture filaments of the present disclosure is primarily a matter of surgeon preference for the surgical procedure to be performed. In some exemplary embodiments, a length of the suture filament can be in the range of about 0.2 meters to about 5 meters.

The devices, systems, and methods disclosed herein can be used in minimally-invasive surgery and/or open surgery. While the devices and methods disclosed herein are generally described in the context of orthopedic surgery on a human patient, it will be appreciated that the methods and devices disclosed herein can be used in any of a variety of surgical procedures with any human or animal subject, or in non-surgical procedures. Additionally, while the methods disclosed herein are generally described in the context of soft tissue repair, repairs of one or more other types of anatomy can be done with aspects of the present disclosure, for example harder tissues such as cartilage or bone, using for example, an opening (e.g., pre-formed, existing, or formed by an inserter configured to form an opening in bone) or through other objects disposed in the body (e.g., a graft, implant, ligament, muscle, etc.)

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc. In some example, the sealed container or other packaging holds an inserter and suture construct that are shipped with the suture construct preloaded on the inserter in the sealed container and/or otherwise configured to allow for the construct to be easily loaded onto the inserter, such as by having an adjustable opening of an adjustable loop open large enough to allow the inserter to be placed within the opening and the loop collapsed to couple the two components together.

The embodiments of the present disclosure described above are intended to be merely exemplary; numerous variations and modifications will be apparent to those skilled in the art. One skilled in the art will appreciate further features and advantages of the disclosure based on the above-described embodiments. Accordingly, the disclosure is not to be limited by what has been particularly shown and described. All publications and references cited herein are expressly incorporated herein by reference in their entirety.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A surgical repair system, comprising:
a suture construct formed from a suture filament, the suture construct including a first tail, a second tail, and an adjustable loop, an opening of the adjustable loop being defined by the second tail being slidably disposed within the first tail such that applying tension to the second tail collapses the opening of the adjustable loop, and
an inserter having a proximal handle, a coupling region, and a distal end, the distal end including a needle, the coupling region being configured to retain the adjustable loop at the coupling region during insertion of the needle through a target tissue when the adjustable loop is collapsed around the coupling region.

2. The surgical repair system of claim 1, wherein the first tail comprises an eyelet formed therein, with the second tail slidably disposed through the eyelet.

3. The surgical repair system of claim 1, wherein the suture filament is a braided suture, and the braided suture is bifurcated at a location at which the second tail is slidably disposed within the first tail.

4. The surgical repair system of claim 1, wherein the coupling region of the inserter comprises a reduced diameter section of an outer surface of the inserter.

5. The surgical repair system of claim 4, wherein the reduced diameter section defines at least one of a proximal transition section or a distal transition section having a chamfered edge disposed between two different diameter sections of the inserter.

6. The surgical repair system of claim 1, wherein the first tail and the second tail are part of a single length of the suture filament.

* * * * *